(12) United States Patent
Beyer et al.

(10) Patent No.: US 8,206,943 B1
(45) Date of Patent: Jun. 26, 2012

(54) ASSAY FOR PCSK9 INHIBITORS

(75) Inventors: Brian M. Beyer, Matawan, NJ (US);
Thomas Hesson, Burlington, MA (US);
Hung V. Le, Rockaway, NJ (US);
Andrew J. Prongay, Billerica, MA (US); Krishna Kalghatgi, Westborough, MA (US); Jennifer Joanne Gesell, Allentown, NJ (US); Richard N. Ingram, Scotch Plains, NJ (US);
Michael R. Ziebell, Arlington, MA (US)

(73) Assignee: Schering Corporation, Kenilworth, NJ (US)

( * ) Notice: Subject to any disclaimer, the term of this patent is extended or adjusted under 35 U.S.C. 154(b) by 438 days.

(21) Appl. No.: 12/493,752

(22) Filed: Jun. 29, 2009

Related U.S. Application Data

(60) Provisional application No. 61/076,879, filed on Jun. 30, 2008.

(51) Int. Cl.
*C12Q 1/37* (2006.01)

(52) U.S. Cl. .......................................... 435/23

(58) Field of Classification Search ............. 435/23
See application file for complete search history.

(56) References Cited

U.S. PATENT DOCUMENTS

| | | | |
|---|---|---|---|
| 7,723,342 B2 | 5/2010 | Palani et al. | |
| 2011/0033465 A1 | 2/2011 | Hedrick et al. | |

FOREIGN PATENT DOCUMENTS

| | | |
|---|---|---|
| WO | WO2008057457 A2 | 5/2008 |
| WO | WO2008057458 A2 | 5/2008 |
| WO | WO2008057459 A2 | 5/2008 |
| WO | WO2008063382 A2 | 5/2008 |
| WO | WO2008118386 A2 | 10/2008 |
| WO | WO2008133647 A2 | 11/2008 |
| WO | WO2009055783 A2 | 4/2009 |
| WO | WO2009100297 A1 | 8/2009 |
| WO | WO2009100318 A1 | 8/2009 |
| WO | WO2009143367 A2 | 11/2009 |
| WO | WO2010068526 A1 | 6/2010 |
| WO | WO2011037791 A1 | 3/2011 |
| WO | WO2011053665 A1 | 5/2011 |
| WO | WO2011053743 A1 | 5/2011 |
| WO | WO2011053759 A1 | 5/2011 |
| WO | WO2011053783 A2 | 5/2011 |

OTHER PUBLICATIONS

Piper et al., Structure, 15, 545-552, May 2007.*
Poirier et al., The Proprotein Convertase PCSK9 Induces the Degradation of Low Density Lipoprotein Receptor (LDLR) and Its Closest Family Members VLDLR and ApoER2. The Journal of Biological Chemistry vol. 283, No. 4, pp. 2363-2372 (2008).
Benjannet et al., NARC-1/PCSK9 and its natural mutants: zymogen cleavage and effects on the low density lipoprotein (LDL) receptor and LDL cholesterol. J Biol Chem 279(47): 48865-75 (2004).
Cunningham et al., Structural and biophysical studies of PCSK9 and its mutants linked to familial hypercholesterolemia. Nat Struct Mol Biol 14(5):413-9 (2007).

\* cited by examiner

*Primary Examiner* — Maryam Monshipouri

(57) ABSTRACT

The present invention provides methods for identifying modulators of PCSK9, for example, using a variety of assay formats. Inhibitors of PCSK9 can be used for example, to treat diseases such as hyperlipidemia and related disorders.

20 Claims, 10 Drawing Sheets

ASSAY FOR PCSK9 INHIBITORS

This application claims the benefit of U.S. provisional patent application No. 61/076,879; filed Jun. 30, 2008, which is herein incorporated by reference in its entirety for all purposes.

FIELD OF THE INVENTION

The present invention relates, generally, to methods for identifying inhibitors of PCSK9.

BACKGROUND OF THE INVENTION

Proprotein convertase subtilisin kexin type 9 (PCSK9) is a serine protease recognized for involvement in the regulation of levels of low-density lipoprotein receptor (LDL-R) protein. In vitro experiments have shown that the addition of PCSK9 to HepG2 cells lowers the levels of the cell surface LDL-R. In addition to this observation, experiments with mice have demonstrated that increasing the concentration of PCSK9 in blood plasma results in a decrease in LDL-R protein in the liver. In addition to PCSK9 mouse knockouts having increased levels of LDL-R in the liver, various PCSK9 mutations have been identified (in several species) that result either in increased or decreased plasma levels of LDL. Experiments have demonstrated a specific interaction between PCSK9 and LDL-R and that the proteins co-immunofluoresce throughout the endosomal pathway.

There is an interest in the art in developing inhibitors of PCSK9 since this gene is a valuable target for treatment of lipid disorders such as hyperlipidemia. The present invention addresses this need by providing a new method for inhibiting proteolytic cleavage and activation of PCSK9.

SUMMARY OF THE INVENTION

The present invention provides a method for identifying an inhibitor of PCSK9 comprising incubating a mixture (e.g., at about 25° C. in 25 mM Hepes pH 7.5, 150 mM NaCl, 10% glycerol and 1 mM EDTA.) comprising a polypeptide comprising a PCSK9 Pro-Cat-domain under conditions which allow autoproteolytic cleavage of the polypeptide between the Pro-domain the Cat-domain in the presence of a substance to be tested for the presence of said inhibitor; and determining generation of said Pro-domain or said Cat-domain, or both, wherein the substance is identified as the inhibitor if said generation of said domain(s) occur(s) at a lower level than that observed in the absence of said substance. In an embodiment of the invention, detection of said Pro-domain or Cat-domain is performed by chromatographically separating the polypeptides in said mixture and analyzing said separated polypeptides. In an embodiment of the invention, detection of said Pro-domain or Cat-domain is performed by mass spectroscopically analyzing the polypeptides in said mixture. In an embodiment of the invention, detection of said Pro-domain or Cat-domain is performed by matrix-assisted laser desorption/ionization mass spectrometrically analyzing the polypeptides in said mixture. In an embodiment of the invention, the mixture is chromatographically separated on a hydrophobic interaction column or is separated using a high performance liquid chromatography system. In an embodiment of the invention, eluate from said chromatographic separation is analyzed spectrophotometrically wherein absorbance of light at 214 nm wavelength is measured. In an embodiment of the invention, detection of said Pro-domain and Cat-domain is performed by performing SDS-PAGE analysis of polypeptides in said mixture. In an embodiment of the invention, detection of said Pro-domain and Cat-domain is performed by performing SDS microchip electrophoresis. In an embodiment of the invention, said Pro-Cat-domain polypeptide comprises the amino acid sequence: QED-EDGDYEELVLALRSEEDGLAEAPEHGT-TATFHRCAKDPWRLPGTYVVVL-KEETHLSQSERTARRLQAQAARRGY LTKILHVFHGLLPGFLVKMSGDLLELA-LKLPHVDYIEEDSSVFAQSIPWNLERIT-PPRYRADEYQPPDGGSLVEVYL LDTSIQS-DHREIEGRVMVTDFENVPEEDGTRFHRQASKCDSHG-THLAGVVSGRDAGVAKGASMRSLRVLNCQGKGTV SGTLIGLEFIRKSQLVQPVGPLVVLL-PLAGGYSRVLNAACQRLARAGVV-LVTAAGNFRDDACLYSPASAPEVITVGA TNAQDQPVTLGTLGTNFGRCVDLFAPGE-DIIGASSDCSTCFVSQSGTSQAAAHVA-GIAAMMLSAEPELTLAELRQRL IHFSAKDVINEAWF-PEDQRVLTPNLVAALPPSTHGAGWQ (SEQ ID NO: 10)

The present invention provides a method for identifying a substance for member selected from the group consisting of reducing total cholesterol level, reducing low density lipoprotein cholesterol level, reducing apolipoprotein B level, reducing total cholesterol/high density lipoprotein ratio and reducing low density lipoprotein/high density lipoprotein ratio; or for treating or preventing a medical disorder selected from the group consisting of hypercholesterolemia, hyperlipidemia, hypertriglyceridaemia, sitosterolemia, atherosclerosis, arteriosclerosis, coronary heart disease, vascular inflammation or treating and xanthoma comprising identifying an inhibitor of PCSK9 by the method for identifying a PCSK9 inhibitor discussed above.

In an embodiment of the invention, any of the screening assays herein are optionally performed in association with a negative-control assay comprising incubating a mixture comprising a polypeptide comprising a PCSK9 Pro-Cat-domain under conditions which allow autoproteolytic cleavage of the polypeptide between the Pro-domain the Cat-domain in the presence of a substance known not to be an inhibitor of PCSK9 autoproteolysis; and determining generation of said Pro-domain or said Cat-domain, or both; wherein the quantity of Pro-domain or Cat-domain indicates the maximum amount of proteolysis. For example, in an embodiment of the invention, said maximum amount of proteolysis is compared to the level than is observed in the absence of said substance; and wherein the substance is identified as the inhibitor if said generation of said domain(s) occur(s) at a lower level than that the maximum amount of proteolysis observed in the negative-control assay.

In an embodiment of the invention, any of the screening assays herein are optionally performed in association with a positive-control assay comprising incubating a mixture comprising a polypeptide comprising a PCSK9 Pro-Cat-domain under conditions which allow autoproteolytic cleavage of the polypeptide between the Pro-domain the Cat-domain in the presence of a positive-control substance known to be an inhibitor of PCSK9 autoproteolysis; and determining generation of said Pro-domain or said Cat-domain, or both, wherein the assay is determined to be functioning properly if generation of said domain(s) occur(s) at a lower level than that observed in the absence of said positive-control substance.

DETAILED DESCRIPTION OF THE INVENTION

Figure 1:
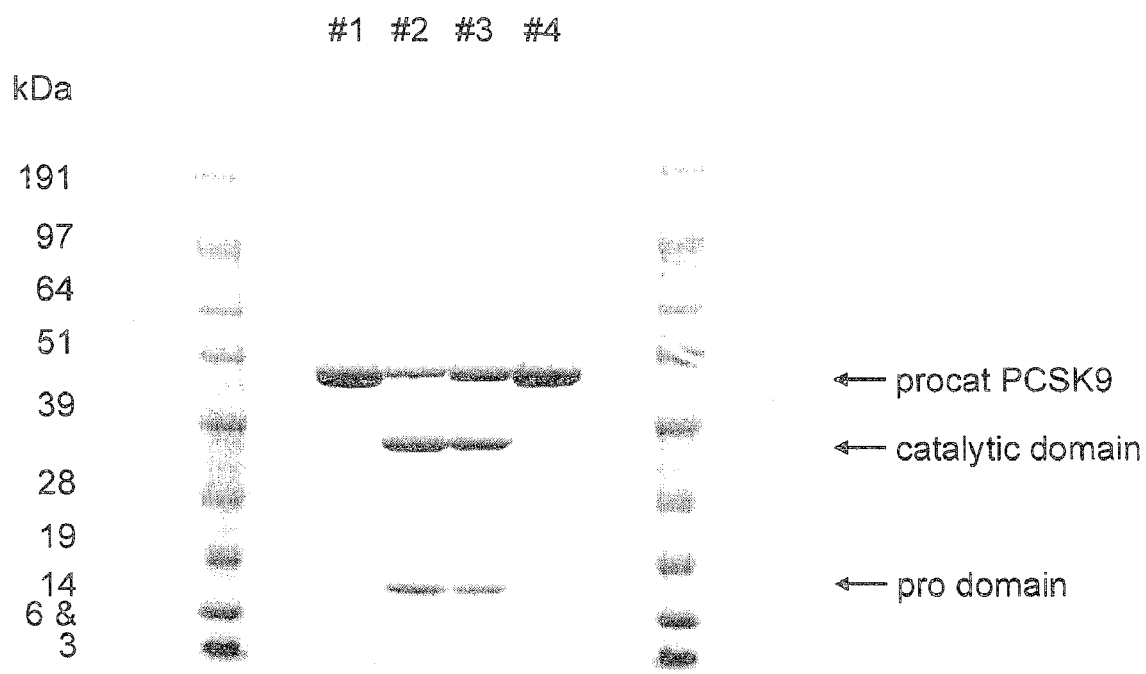
FIG. 1: SDS-PAGE analysis of PCSK9 autoproteolysis assay. PCSK9 (8 µM) was incubated at 25° C. in 25 mM Hepes pH 7.5, 150 mM NaCl, 1 mM EDTA, 10% glycerol and 4% DMSO. Lane 1=unprocessed material; Lane 2=processed for 23 hours; Lane 3=processed for 6 hours; and Lane 4=processed for 6 hours with 77 µM inhibitory compound.

One method for targeting PCSK9 is with an inhibitor that antagonizes proteolytic cleavage, into a Pro-domain and a Cat-domain, and activation of PCSK9. Proteolytic cleavage of PCSK9 is required for the proper folding and secretion of the protein. Inhibition of this processing step provides a powerful tool for the identification of therapeutic PCSK9 inhibitors. Candidate inhibitors that may be tested using the assays of the present invention include, for example, antibodies (e.g., anti-PCSK9 antibodies), small organic molecules and peptides.

Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook, et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel, et al. (eds.), *Current Protocols in Molecular Biology*, John Wiley & Sons, Inc. (1994).

A "polynucleotide", "nucleic acid" or "nucleic acid molecule" includes DNA and RNA, including single-stranded molecules, double-stranded molecules and others.

A "polynucleotide sequence", "nucleic acid sequence" or "nucleotide sequence" is a series of nucleotide bases (also called "nucleotides") in a nucleic acid, such as DNA or RNA, and means any chain of two or more nucleotides.

A "coding sequence" or a sequence "encoding" an expression product, such as an RNA, polypeptide, protein, or enzyme, is a nucleotide sequence that, when expressed, results in production of the product.

The term "gene" includes a DNA that codes for or corresponds to a particular sequence of ribonucleotides or amino acids which comprise all or part of one or more RNA molecules, proteins or enzymes, and may or may not include regulatory DNA sequences, such as promoter sequences, which determine, for example, the conditions under which the gene is expressed. Genes may be transcribed from DNA to RNA which may or may not be translated into an amino acid sequence.

As used herein, the term "oligonucleotide" refers to a nucleic acid, generally of no more than about 100 nucleotides (e.g., 30, 40, 50, 60, 70, 80, or 90), that may be hybridizable to a genomic DNA molecule, a cDNA molecule, or an mRNA molecule encoding a gene, mRNA, cDNA, or other nucleic acid of interest. Oligonucleotides can be labeled, e.g., by incorporation of $^{32}$P-nucleotides, $^{3}$H-nucleotides, $^{14}$C-nucleotides, $^{35}$S-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of the gene, or to detect the presence of nucleic acids. Generally, oligonucleotides are prepared synthetically, e.g., on a nucleic acid synthesizer.

A "protein sequence", "peptide sequence" or "polypeptide sequence" or "amino acid sequence" includes a series of two or more amino acids in a protein, peptide or polypeptide.

The terms "isolated polynucleotide" or "isolated polypeptide" include a polynucleotide (e.g., RNA or DNA molecule, or a mixed polymer) or a polypeptide, respectively, which are partially or fully separated from other components that are normally found in cells or in recombinant DNA expression systems. These components include, but are not limited to, cell membranes, cell walls, ribosomes, polymerases, serum components and extraneous genomic sequences.

An isolated polynucleotide or polypeptide will, in an embodiment of the invention, be an essentially homogeneous composition of molecules but may contain some heterogeneity.

"Amplification" of DNA as used herein includes the use of polymerase chain reaction (PCR) to increase the concentration of a particular DNA sequence within a mixture of DNA sequences. For a description of PCR see Saiki, et al., Science (1988) 239:487.

The term "host cell" includes any cell of any organism that is selected, modified, transfected, transformed, grown, or used or manipulated in any way, for the production of a substance by the cell, for example the expression or replication, by the cell, of a gene, a DNA or RNA sequence or a protein. Host cells include Chinese hamster ovary (CHO) cells, murine macrophage J774 cells or any other macrophage cell line and human intestinal epithelial Caco2 cells. For example, the BL21 *E. coli* host cell comprises the T7 expression system and includes the Ion and ompT proteases (see e.g., Studier, F. W. and Moffatt, B. A. (1986) J. Mol. Biol. 189, 113; Rosenberg, A. H., Lade, B. N., Chui, D., Lin, S., Dunn, J. J. and Studier, F. W. (1987) Gene 56, 125; Studier, F. W., Rosenberg, A. H., Dunn, J. J. and Dubendorff, J. W. (1990) Meth. Enzymol. 185, 60-89; Studier, F. W. (1991) J. Mol. Biol. 219, 37-44; Zhang, X. and Studier, F. W. (1997) J. Mol Biol. 269, 10-27; Derman, A. I., Prinz, W. A., Belin, D., and Beckwith, J. (1993) Science 262, 1744-1747; Wood, W. B. (1966) J. Mol. Biol. 16, 118-133; Leahy, D. J., Hendrickson, W. A., Aukhil, I., and Erickson, H. P. (1992) Science 258, 987-991; Phillips, T. A., Van Bogelen, R. A., and Neidhardt, F. C. (1984) J. Bacteriol. 159, 283-287; Prinz, W. A., Aslund, F., Holmgren, A., and Beckwith, J. (1997) J. Biol. Chem. 272, 15661-15667; Stewart, E. J., Aslund, F. and Beckwith, J. (1998) EMBO J. 17, 5543-5550; Bessette, P. H., Aslund, F., Beckwith, J. and Georgiou, G. (1999) Proc. Natl. Acad. Sci. 96, 13703-13708; Kane, J. F (1995) Curr. Opin. Biotechnol. 6, 494-500; Kurland, C. and Gallant, J. (1996) 7: 489-493; Brinkmann, U., Mattes, R. E. and Buckel, P. (1989) Gene 85, 109-114; Seidel, H. M., Pompliano, D. L. and Knowes, J. R. (1992) Biochemistry 31, 2598-2608; Rosenberg, A. H., Goldman, E., Dunn, J. J., Studier F. W. and Zubay, G. (1993) J. Bacteriol. 175, 716-722; or Del Tito, B. J., Ward, J. M.; Hodgson, J. (1995) J. Bacteriol. 177, 7086-7091; U.S. Pat. Nos. 4,952,496, 5,693,489 and 5,869,320; Davanloo, P., et al., (1984) Proc. Natl. Acad. Sci. USA 81: 2035-2039; Studier, F. W., et al., (1986) J. Mol. Biol. 189: 113-130; Rosenberg, A. H., et al., (1987) Gene 56: 125-135; and Dunn, J. J., et al., (1988) Gene 68: 259.). BL21 (DE3) lacks the Ion and ompT proteases. BL21(DE3)pLysS lacks the Ion and ompT proteases and is resistant to 34 µg/ml chloramphenicol.

The nucleotide sequence of a nucleic acid may be determined by any method known in the art (e.g., chemical sequencing or enzymatic sequencing). "Chemical sequencing" of DNA includes methods such as that of Maxam and Gilbert (1977) (Proc. Natl. Acad. Sci. USA 74:560), in which DNA is randomly cleaved using individual base-specific reactions. "Enzymatic sequencing" of DNA includes methods such as that of Sanger (Sanger, et al., (1977) Proc. Natl. Acad. Sci. USA 74:5463).

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

In general, a "promoter" or "promoter sequence" is a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences or with a nucleic acid of the invention. Promoters which may be used to control gene expression include, but are not limited to, cytomegalovirus (CMV) promoter (U.S. Pat. Nos. 5,385,839 and 5,168,062), the SV40 early promoter region (Benoist, et al., (1981) Nature 290:304-310), the promoter contained in the 3' long terminal repeat of Rous sarcoma virus (Yamamoto, et al., (1980) Cell 22:787-797), the herpes thymidine kinase promoter (Wagner, et al., (1981) Proc. Natl. Acad. Sci. USA 78:1441-1445), the regulatory sequences of the metallothionein gene (Brinster, et al., (1982) Nature 296:39-42); prokaryotic expression vectors such as the β-lactamase promoter (VIIIa-Komaroff, et al., (1978) Proc. Natl. Acad. Sci. USA 75:3727-3731), or the tac promoter (DeBoer, et al., (1983) Proc. Natl. Acad. Sci. USA 80:21-25); see also "Useful proteins from recombinant bacteria" in Scientific American (1980) 242:74-94; and promoter elements from yeast or other fungi such as the Gal 4 promoter, the ADC (alcohol dehydrogenase) promoter, PGK (phosphoglycerol kinase) promoter or the alkaline phosphatase promoter.

A coding sequence is "under the control of", "functionally associated with" or "operably associated with" transcriptional and translational control sequences when the sequences direct RNA polymerase mediated transcription of the coding sequence into RNA, e.g., mRNA, which then may be RNA spliced (if it contains introns) and, optionally, translated into a protein encoded by the coding sequence.

The terms "express" and "expression" include allowing or causing the information in a gene, RNA or DNA sequence to become manifest; for example, producing a protein by activating the cellular functions involved in transcription and translation of a corresponding gene. A DNA sequence is expressed in or by a cell to form an "expression product" such as an RNA (e.g., mRNA) or a protein. The expression product itself may also be said to be "expressed" by the cell.

The term "transformation" means the introduction of a nucleic acid into a cell. The introduced gene or sequence may be called a "clone". A host cell that receives the introduced DNA or RNA has been "transformed" and is a "transformant" or a "clone." The DNA or RNA introduced to a host cell can come from any source, including cells of the same genus or species as the host cell, or from cells of a different genus or species.

The term "vector" includes a vehicle (e.g., a plasmid) by which a DNA or RNA sequence can be introduced into a host cell, so as to transform the host and, optionally, promote expression and/or replication of the introduced sequence. Plasmids are the most commonly used form of vector but all other forms of vectors which serve a similar function and which are, or become, known in the art are suitable for use herein. See, e.g., Pouwels, et al., *Cloning Vectors: A Laboratory Manual*, 1985 and Supplements, Elsevier, N.Y., and Rodriguez et al. (eds.), *Vectors: A Survey of Molecular Cloning Vectors and Their Uses*, 1988, Buttersworth, Boston, Mass.

The term "expression system" includes a host cell and compatible vector which, under suitable conditions, can express a protein or nucleic acid which is carried by the vector and introduced to the host cell. Common expression systems include *E. coli* host cells and plasmid vectors, insect host cells and Baculovirus vectors, and mammalian host cells and vectors. An example of an expression system is the T7 polymerase-based expression system discussed above regarding the BL21 host cells (e.g., as discussed herein).

Expression of nucleic acids encoding the polypeptides of this invention can be carried out by conventional methods in either prokaryotic or eukaryotic cells. Although *E. coli* host cells are employed most frequently in prokaryotic systems, many other bacteria, such as various strains of *Pseudomonas* and *Bacillus*, are known in the art and can be used as well. Suitable host cells for expressing nucleic acids encoding the polypeptides include prokaryotes and higher eukaryotes. Prokaryotes include both gram-negative and gram-positive organisms, e.g., *E. coli* and *B. subtilis*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. A representative vector for amplifying DNA is pBR322 or many of its derivatives (e.g., pUC18 or 19). Vectors that can be used to express the polypeptides include, but are not limited to, those containing the lac promoter (pUC-series); trp promoter (pBR322-trp); Ipp promoter (the pIN-series); lambda-pP or pR promoters (pOTS); or hybrid promoters such as ptac (pDR540). See Brosius et al., "Expression Vectors Employing Lambda-, trp-, lac-, and Ipp-derived Promoters", in Rodriguez and Denhardt (eds.) *Vectors: A Survey of Molecular Cloning Vectors and Their Uses,* 1988, Buttersworth, Boston, pp. 205-236. Many polypeptides can be expressed, at high levels, in an *E. coli*/T7 expression system.

Higher eukaryotic tissue culture cells may also be used for the recombinant production of the polypeptides of the invention. Transformation or transfection and propagation of such cells have become a routine procedure. Examples of useful cell lines include HeLa cells, Chinese hamster ovary (CHO) cell lines, J774 cells, Caco2 cells, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also, usually, contain a selection gene or amplification gene. Suitable expression vectors may be plasmids, viruses, or retroviruses carrying promoters derived, e.g., from such sources as adenovirus, SV40, parvoviruses, vaccinia virus, or cytomegalovirus. Examples of expression vectors include pET-based vectors, pDEST14, pCR®3.1, pcDNA1, pCD (Okayama, et al., (1985) Mol. Cell Biol. 5:1136), pMC1 neo Poly-A (Thomas, et al., (1987) Cell 51:503), pREP8, pSVSPORT and derivatives thereof, and baculovirus vectors such as pAC373 or pAC610.

The present invention also includes use of fusions which include the PCSK9 polypeptides and PCSK9 polynucleotides of the present invention and a second polypeptide or polynucleotide moiety, which may be referred to as a "tag". A tag may, in an embodiment of the invention, be any heterologous protein which comprises an amino acid sequence which does not appear contiguously with that of the PCSK9 sequence to which the tag is appended. The fused polypeptides of the invention may be conveniently constructed, for example, by insertion of a polynucleotide of the invention or fragment thereof into an expression vector. The fusions of the invention may include tags which facilitate purification or detection. Such tags include glutathione-S-transferase (GST), hexahistidine (His6) tags, maltose binding protein (MBP) tags, haemagglutinin (HA) tags, cellulose binding protein (CBP) tags and myc tags. Detectable tags such as $^{32}$P, $^{38}$S, $^{3}$H, $^{99m}$Tc, $^{123}$I, $^{111}$In, $^{68}$Ga, $^{18}$F, $^{125}$I, $^{131}$I, $^{113m}$In, $^{76}$Br, $^{67}$Ga, $^{99m}$Tc, $^{123}$I, $^{111}$In and $^{68}$Ga may also be used to label the polypeptides and polynucleotides of the invention. Fluorescent tags for use in connection with FRET are discussed below. Methods for constructing and using such fusions are very conventional and well known in the art.

Modifications (e.g., post-translational modifications) that occur in a polypeptide often will be a function of how it is made. For polypeptides made by expressing a cloned gene in a host, for instance, the nature and extent of the modifications, in large part, will be determined by the host cell's post-translational modification capacity and the modification signals present in the polypeptide amino acid sequence. For instance, as is well known, glycosylation often does not occur in bacterial hosts such as *E. coli*. Accordingly, when glycosylation is desired, a polypeptide can be expressed in a glycosylating host, generally a eukaryotic cell (e.g., CHO cells). Insect cells often carry out post-translational glycosylations which are similar to those of mammalian cells. For this reason, insect cell expression systems have been developed to express, efficiently, mammalian proteins having native patterns of glycosylation. An insect cell includes any cell derived from an organism of the class Insecta. In an embodiment of the invention, the insect is *Spodoptera* fruigiperda (Sf9 or Sf21) or *Trichoplusia ni* (High 5). Examples of insect expression systems useful, for example, to produce PCSK9 polypeptide, include Bac-To-Bac (Invitrogen Corporation, Carlsbad, Calif.) or Gateway (Invitrogen Corporation, Carlsbad, Calif.). If desired, deglycosylation enzymes can be used to remove carbohydrates attached during production in eukaryotic expression systems.

Other modifications may also include addition of aliphatic esters or amides to the polypeptide carboxyl-terminus. The present invention also includes use of analogs of the PCSK9 polypeptides which contain modifications, such as incorporation of unnatural amino acid residues, or phosphorylated amino acid residues such as phosphotyrosine, phosphoserine or phosphothreonine residues. Other potential modifications include sulfonation, biotinylation, or the addition of other moieties. For example, the PCSK9 polypeptides may be appended with a polymer such as polyethylene glycol (PEG) (e.g., PEG with a molecular weight of 2 kDa, 5 kDa, 10 kDa, 12 kDa, 20 kDa, 30 kDa and 40 kDa), dextran and monomethoxypolyethylene glycol (mPEG).

The present invention contemplates use of superficial or slight modifications to the amino acid or nucleotide sequences which correspond to the polypeptides of the invention. In particular, the present invention contemplates sequence conservative variants of the nucleic acids which encode the polypeptides of the invention. "Sequence-conservative variants" of a polynucleotide sequence are those in which a change of one or more nucleotides in a given codon results in no alteration in the amino acid encoded at that position. Function-conservative variants of the polypeptides of the invention are also contemplated by the present invention. "Function-conservative variants" are those in which one or more amino acid residues in a protein or enzyme have been changed without altering the overall conformation and function of the polypeptide, including, but, by no means, limited to, replacement of an amino acid with one having similar properties. Amino acids with similar properties are well known in the art. For example, polar/hydrophilic amino acids which may be interchangeable include asparagine, glutamine, serine, cysteine, threonine, lysine, arginine, histidine, aspartic acid and glutamic acid; nonpolar/hydrophobic amino acids which may be interchangeable include glycine, alanine, valine, leucine, isoleucine, proline, tyrosine, phenylalanine, tryptophan and methionine; acidic amino acids which may be interchangeable include aspartic acid and glutamic acid and basic amino acids which may be interchangeable include histidine, lysine and arginine.

The present invention includes use of polynucleotides encoding human, chimp, mouse and rat PCSK9 and fragments thereof as well as nucleic acids which hybridize to the polynucleotides. In an embodiment of the invention, the nucleic acids hybridize under low stringency conditions, more preferably under moderate stringency conditions and most preferably under high stringency conditions. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook, et al., supra). The conditions of temperature and ionic strength determine the "stringency" of the hybridization. Stringency of southern blotting conditions can be altered by altering the conditions under which the blot is washed following hybridization. For example, for low stringency, wash the filter twice in 0.2×SSC, 0.1% SDS solution for 10 minutes each at about 25° C.; for moderate stringency, also wash the filter twice in pre-warmed (42° C.) 0.2×SSC, 0.1% SDS solution for 15 minutes each at 42° C.; for high stringency, in addition to the low and moderate stringency washes, also wash the filter twice in pre-warmed (68° C.) 0.1×SSC, 0.1% SDS solution for 15 minutes each at 68° C. for high-stringent wash. In general, SSC is 0.15M NaCl and 0.015M Na-citrate. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al., supra, 9.50-9.51). For hybridization with shorter nucleic acids, i.e., oligonucleotides, the position of mismatches becomes more important, and the length of the oligonucleotide determines its specificity (see Sambrook, et al., supra).

Also included in the present invention are uses of polynucleotides comprising nucleotide sequences and polypeptides comprising amino acid sequences which are at least about 70% identical, preferably at least about 80% identical, more preferably at least about 90% identical and most preferably at least about 95% identical (e.g., 95%, 96%, 97%, 98%, 99%, 100%) to the reference PCSK9 nucleotide and amino acid sequences (e.g., any set forth herein) when the comparison is performed by a BLAST algorithm wherein the parameters of the algorithm are selected to give the largest match between the respective sequences over the entire length of the respective reference sequences. Uses of polypeptides comprising amino acid sequences which are at least about 70% similar, preferably at least about 80% similar, more preferably at least about 90% similar and most preferably at least about 95% similar (e.g., 95%, 96%, 97%, 98%, 99%, 100%) to the reference PCSK9 amino acid sequence when the comparison is performed with a BLAST algorithm wherein the parameters of the algorithm are selected to give the largest match between the respective sequences over the entire length of the respective reference sequences, are also included in the present invention. In addition to the sequence identities discussed herein, the polypeptides of the present invention may also be characterized in that they autoproteolyze between the Pro- and Cat-domains (e.g., between amino acids Q152 and S153); and/or bind to LDL receptor and/or the EGF-A domain of the LDL receptor.

Sequence identity refers to exact matches between the nucleotides or amino acids of two sequences which are being compared. Sequence similarity refers to both exact matches between the amino acids of two polypeptides which are being compared in addition to matches between nonidentical, biochemically related amino acids. Biochemically related amino acids which share similar properties and may be interchangeable are discussed above.

The following references regarding the BLAST algorithm are herein incorporated by reference: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M., et al., (1994) Comput. Appl. Biosci. 10:67-70; ALIGNMENT SCORING SYSTEMS: Dayhoff, M. O., et al., "A model of evolutionary change in proteins." in *Atlas of Protein Sequence and Structure*, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in *Atlas of Protein Sequence and Structure*, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in *Theoretical and Computational Methods in Genome Research* (S. Suhai, ed.), (1997) pp. 1-14, Plenum, New York.

PCSK9

The methods of the present invention can be used to identify antagonists of PCSK9 from any organism, including human PCSK9. The meaning of the term "PCSK9" is known in the art. In an embodiment of the invention, human PCSK9 comprises the following sequence:
HUMAN gi|31317307|ref|NP_777596.2| proprotein convertase subtilisin/kexin type 9 preproprotein [*Homo sapiens*]
MGTVSSRRSWWPLPLLLLLLLLGPAGARA
QEDEDGDYEELVLALRSEEDGLAEAPEHGTTATFHR-
CAKDPWRLPGTYVVVLKEETHLSQSERTARRLQAQ-
AARRGYLTKILHVFHGLLPGFLVKMSGDLLELALKL-
PHVDYIEEDSSVFAQ
SIPWNLERITPPRYRADEYQPPDGGSLVEVYLLDTSI-
QSDHREIEGRVMVTDFENVPEEDGTRFHRQASKCDS-
HGTHLAGVVSGRDAGVAKGASMRSLRVLNCQGKGT-
VSGTLIGLEFIRKSQLVQPVGPLVVLLPLAGGYSRVL-
NAACQRLARAGVVLVTAAGNFRDDACLYSPASAPE-
VITVGATNAQDQPVTLGTLGTNFGRCVDLFAPGEDII-
GASSDCSTCFVSQSGTSQAAAHVAGIAAMMLSAEPE-
LTLAELRQRLIHFSAKDVINEAWFPEDQRVLTPNLVA-
ALPPSTHGAGWQLFCRTVWSAHSGPTRMATAVARC-
APDEELLSCSSFS RSGKRRGERMEAQG-
GKLVCRAHNAFGGEGVYAIARCCLL-
PQANCSVHTAPPAEASMGTRVHCHQQGHVLT
GCSSHWEVEDLGTHKPPVLRPRGQPN-
QCVGHREASIHASCCHAPGLECKVKEH-
GIPAPQEQVTVACEEGW TLTGCSALPGTSHVL-
GAYAVDNTCVVRSRDVSTTGSTSEGAVTAVAICCRSR-
HLAQASQELQ (SEQ ID NO: 1). The catalytic domain (Cat-domain) is single underscored. The mature propeptide (Pro-domain) is double underscored. The Pro-Cat-domain includes amino acids 31-454 of human PCSK9. The present invention also comprises use of PCSK9 comprising one or more of the following mutations: R46L, S127R, D374Y, R215H, G236S, A245T, R272Q, N354I.

A Pro-Cat polypeptide includes at least the Pro-domain and the Cat-domain, for example, full length PCSK9 or a mature fragment of PCSK9 lacking the signal sequence (e.g., amino acids 1-30 of human PCSK9).

In an embodiment of the invention, chimpanzee PCSK9 comprises the following sequence:
CHIMP gi|114556790|ref|XP_001154126.1| PREDICTED: proprotein convertase subtilisin/kexin type 9 [Pan troglodytes] MGTVSSRRSWWPLPLLLLLLLLLGPAGARA QEDEDGLAEAPEHGTTATFHRCAKDPWRLPGTYVV-VLKEETHLSSERTARRLQAQAARRGYLTKILHVFHG-LLPGFLVKMSGDLLELALKLPHVDYIEEDSSVFAQ SIPWNLERITPPRYRADEYQPPDGGSLVEVYLLDTSI-QSDHREIEGRVMVTDFENVPEEDGTREHRQASKCD-SHGTHLAGVVSGRDAGVAKGASMRSLRVLNCQGK-GTVSGTLIGLEFIRKSQLVQPVGPLVVLLPLAGGYSR-VLNAACQRLARAGVVLVTAAGNFRDDACLYSPASA-PEVITVGATNAQDQPVTLGTLGTNFGRCVDLFAPGE-DIIGASSDCSTCFVSQSGTSQAAAHVAGIAAMMLSA-EPELTLAELRQRLIHFSAKDVINEAWFPEDQRVLTPN-LVAALPPSTHCAGWQLFCRTVWSAHSGPTRMATAV-ARCAPDEELLSCSSFSRSGKRRGERMEAQGG KLVCRAHNAFGGEGVYAIARCCLL-PQANCSIHTAPPAEAGMGTRVHCHQQGH-VLTGCSSHWEVEDLGTHK PPMLRPRGQPNQCVGH-REASIHASCCRAPGLECK VKEHGIPAPQEQVTVACEE-GWTLTGCSALPGTSHVL GAYAVDNTCVVRSRD-VSTAGSTSEEAVAAVAICCRSRHLAQASQELQ (SEQ ID NO: 2). The catalytic domain (Cat-domain) is single underscored. The mature propeptide (Pro-domain) is double underscored.

In an embodiment of the invention, mouse PCSK9 comprises the following sequence:
MOUSE gi|23956352|ref|NP_705793.1| proprotein convertase subtilisin/kexin type 9 [*Mus musculus*] MGTHCSAWL-RWPLLPLLPPLLLLLLLLCPTGAGA QDEDGDYEELMLALPSQEDGLADEAAHVATATFRR-CSKEAWRLPGTYIVVLMEETQRLQIEQTAHRLQTRA-ARRGYVIKVLHIFYDLFPGFLVKMSSDLLGLALKLP-HVEYIEEDSFVFAQ SIPWNLERIIPAWHQTEEDRSPDGSSQVEVYLLDTSI-QGAHREIEGRVTITDFNSVPEEDGTRFHRQASKCDS-HGTHLAGVVSGRDAGVAKGTSLHSLRVLNCQGKGT-VSGTLIGLEFIRKSQLIQPSGPLVVLLPLAGGYSRILN-AACRHLARTGVVLVAAAGNFRDDACLYSPASAPEVI-TVGATNAQDQPVTLGTLGTNFGRCVDLFAPGKDIIG-ASSDCSTCFMSQSGTSQAAAHVAGIVARMLSREPTL-TLAELRQRLIHFSTKDVINMAWFPEDQQVLTPNLVAT-LPPSTHETGGQLLCRTVWSAHSGPTRTATATARCAPE-EELLSCS SFSRSGRRRGDWIEAIGGQQVCK-ALNAFGGEGVYAVARCCLVPRANC-SIHNTPAARAGLETHVHCHQKDH VLTGCSFHWEV-EDLSVRRQPALRSRRQPGQCVGHQAASVYASCCHA-PGLECKIKEHGISGPSEQVTVACE AGWTLTGCNVLP-GASLTLGAYSVDNLCVARVHDT-ARADRTSGEATVAAAICCRSRPSAKASWVQ (SEQ ID NO: 3). The catalytic domain (Cat-domain) is single underscored. The mature propeptide (Pro-domain) is double underscored.

In an embodiment of the invention, rat PCSK9 comprises the following sequence:
RAT gi|77020250|ref|NP_954862.2| proprotein convertase subtilisin/kexin type 9 [*Rattus norvegicus*] MGIRCSTWLR-WPLSPQLLLLLLLCPTGSRA QDEDGDYEELMLALPSQEDSLVDEASHVATATFRRC-SKEAWRLPGTYVVVLMEETQRLQVEQTAHRLQTW-AARRGYVIKVLHVFYDLFPGFLVKMSSDLLGLALK-LPHVEYIEEDSLVFAQ SIPWNLERIIPAWQQTEEDSSPDGSSQVEVYLLDTSI-QSGHREIEGRVTITDFNSVPEEDGTRFHRQASKCDS-HGTHLAGVVSGRDAGVAKGTSLHSLRVLNCQGKGT-VSGTLIGLEFIRKSQLIQPSGPLVVLLPLAGGYSRILN-TACQRLARTGVVLVAAAGNFRDDACLYSPASAPEVIT-VGATNAQDQPVTLGTLGTNFGRCVDLFAPGKDIIGA-SSDCSTCYMSQSGTSQAAAHVAGIVAMMLNRDPAL-TLAELRQRLILFSTKDVINMAWFPEDQRVLTPNRVAT-LPPSTQETGGQLLCRTVWSAHSGPTRTATATARCAP-EEELLSCSSFSR SGRRRGDRIEAIGGQQVCK-ALNAFGGEGVYAVARCCLLPRVNC-SIHNTPAARAGPQTPVHCHQKDHVLTG CSFHW-EVENLRAQQQPLLRSRHQPGQCVGHQEASVHASC-CHAPGLECKIKEHGIAGPAEQVTVACEAGWT LTGCN-VLPGASLPLGAYSVDNVCVARIRDA-GRADRTSEEATVAAAICCRSRPSAKASWVHQ (SEQ ID NO: 4). The catalytic domain (Cat-domain) is single underscored. The mature propeptide (Pro-domain) is double underscored.

Proteolytic cleavage of PCSK9 occurs at the junction between the Pro- and Cat-domains. For example, between Q152 and S153 of human PCSK9.

Assay Formats

The present invention provides methods by which a PCSK9 inhibitor is identified based upon its ability to inhibit PCSK9-mediated autoproteolysis. Methods of the present invention include those in which a candidate inhibitor is incubated in the presence of PCSK9 and PCSK9 autoproteolysis is determined; wherein the candidate inhibitor is identified as an inhibitor of PCSK9 if autoproteolysis in the presence of the inhibitor occurs to a lesser degree than in the absence of the candidate inhibitor. The scope of the present invention encompasses any method by which such a determination is made.

The Pro-domain and the Cat-domain may remain tightly associated following cleavage of a ProCat polypeptide. Thus, any of the assays described herein may require the additional step, when appropriate, of treating the Pro-domain/Cat-domain complex so as to release the two moieties. For example, treatment of the complex with a denaturant such as urea may release the moieties.

For example, the present invention includes a method for identifying an inhibitor of PCSK9 comprising:
(i) incubating a mixture comprising a polypeptide including a PCSK9 Pro-Cat domain under conditions which allow autoproteolytic cleavage of the polypeptide between the Pro-domain and the Cat-domain in the presence of a substance to be tested for the presence of said inhibitor (e.g., candidate substance); and
(ii) determining generation of said Pro-domain and/or said Cat-domain;
wherein the substance is identified as the inhibitor if said generation of said domain(s) occur(s) at a lower level than that observed in the absence of said substance.

In an embodiment of the invention, a "lower level" refers to a lower rate of generation of Pro- and/or Cat-domain and/or generation of a lower amount of Pro- and/or Cat-domain after a given period of time.

In an embodiment of the invention, "determining" a domain (e.g., Pro- or Cat-) refers to measuring or quantitating the rate of generation of the domain and/or measuring or quantitating the overall amount of domain generated over a given period of time.

Methods by which PCSK9 autoproteolysis is determined include, for example, those wherein the generation of PCSK9 proteolytic fragments is directly detected. For example, in an embodiment of the invention, the assay mixture is analyzed visually following SDS-PAGE separation of the components of the mixture and protein staining of the SDS-PAGE gel (e.g., with Coomassie Brilliant Blue stain or silver stain).

SDS-PAGE stands for sodium dodecyl sulfate (SDS) polyacrylamide gel electrophoresis (PAGE) and is useful for molecular weight analysis of proteins. SDS is a detergent that dissociates and unfolds oligomeric proteins into its subunits. The SDS binds to the polypeptides to form complexes with fairly constant charge to mass ratios. The electrophoretic migration rate through a gel is therefore determined by the size of the complexes. Molecular weights are determined by simultaneously running marker proteins of known molecular weight. SDS-PAGE analysis was initially described by Laemmli (Nature 227: 680-685 (1970)) which is herein incorporated by reference in its entirety. Methods for making and running and analyzing such gels are well within the knowledge and skill in the art.

Alternatively, the assay mixture may be analyzed following chromatographic separation of the mixture's components. For example, the assay mixture may be subjected to separation on an HPLC (high performance liquid chromatography) column wherein the eluate is analyzed for the presence of degradation product spectrophotometrically (e.g., absorbance of UV light (e.g., at 214 nm wavelength) or fluorescently).

For example, the present invention includes a method for identifying an inhibitor of PCSK9 comprising:
(i) incubating a mixture comprising a polypeptide including a PCSK9 Pro-Cat-domain under conditions which allow autoproteolytic cleavage of the polypeptide between the Pro-domain and the Cat-domain in the presence of a substance to be tested for the presence of said inhibitor (e.g., candidate substance);
(ii) chromatographically fractionating the mixture, e.g., using a column, e.g., using a high performance liquid chromatography (HPLC) apparatus; and
(iii) analyzing the eluate from said fractionation (e.g., spectrophotometrically at 214 nm) and determining, therefrom, the quantity of PCSK9 Pro- and/or Cat-domain generated; wherein the substance is identified as the inhibitor if said generation of said domain(s) occur(s) at a lower level than that observed in the absence of said substance.

Alternatively, the mixture may be analyzed by high throughput liquid chromatography. High throughput liquid chromatography relates to the use of cartridges comprising miniature columns which include various chromatographic resins (e.g., C4). Multiple columns may run and be analyzed simultaneously on such an apparatus. Again, the eluate from such a column may be analyzed for the presence of the proteolytic degradation products spectrophotometrically (e.g., absorbance of UV light or fluorescently). Such apparatuses are commercially available, for example, the Nanostream CL System. For example, the present invention includes a method for identifying an inhibitor of PCSK9 comprising:
(i) incubating a mixture comprising a polypeptide including a PCSK9 Pro-Cat domain under conditions which allow autoproteolytic cleavage of the polypeptide between the Pro-domain and the Cat-domain in the presence of a substance to be tested for the presence of said inhibitor (e.g., candidate substance) (e.g., wherein each mixture comprises a separate candidate substance);
(ii) chromatographically fractionating the mixture, e.g., using a column or column cartridge, e.g., using a high performance liquid chromatography apparatus; and
(iii) analyzing the eluate from said fractionation (e.g., spectrophotometrically at 214 nm) and determining, therefrom, the quantity of PCSK9 Pro- and/or Cat-domain generated; wherein the substance is identified as the inhibitor if said generation of said domain(s) occur(s) at a lower level than that observed in the absence of said substance.

Mass spectrometry (e.g., matrix-assisted laser desorption/ionization MALDI mass spectrometry) based assays are also within the scope of the present invention. Mass spectrometry based assays detect the generation of a Pro- and/or Cat-domain peptides by mass spectrometric analysis of the reaction mixture. In an embodiment of the invention, such a method comprises the steps:
(i) incubating a mixture comprising a polypeptide including a PCSK9 Pro-Cat-domain under conditions which allow autoproteolytic cleavage of the polypeptide between the Pro-domain and the Cat-domain in the presence of a substance to be tested for the presence of said inhibitor (e.g., candidate substance); and
(ii) analyzing the composition of the mixture in a mass spectrometer (e.g., MALDI mass spectroscopy) and identifying the quantity of PCSK9 Cat- and/or Pro-domain in the mixture; wherein the substance is identified as the inhibitor if said generation of said domain(s) occur(s) at a lower level than that observed in the absence of said substance. In an embodiment of the invention, the analysis of the mass spectrometry includes generation of a plot of intensity vs. mass (m)-to-charge (z) ratio (m/z). In an embodiment of the invention, the quantity of domain in the mixture is proportional to the magnitude of the appropriate peak in the plot.

Another assay format is FRET (fluorescence resonance energy transfer). FRET takes place when the fluorescence emission band of one molecule (donor) overlaps with an excitation band of a second (acceptor) that is within, e.g., about 10-100 Å of the donor. At an appropriate constant total concentration of free and associated FRET pairs, the emission of the FRET donor is inversely proportional to the mole fraction of associated donor and acceptor molecules. For example, in such a format, the Pro-domain can be labeled with a FRET donor and the Cat-domain labeled with a FRET acceptor. When cleavage of the protein into separate domains occurs, fluorescence by the donor will be observed to increase in the reaction assay. Generally, donor and acceptor molecules must be in close proximity (typically about 10-100 Å) and the absorption spectrum of the acceptor must overlap the fluorescence emission spectrum of the donor.

For example, in an embodiment of the invention, such a FRET-based method would include the following steps:
(i) incubating a mixture comprising a polypeptide comprising a PCSK9 Pro-Cat-domain wherein the Pro-domain is labeled with a FRET donor or acceptor and the Cat-domain is labeled with the other (i.e., donor or acceptor); under conditions which allow autoproteolytic cleavage of the polypeptide between the Pro-domain and the Cat-domain in the presence of a substance to be tested for the presence of said inhibitor; and
(ii) determining generation of said Pro-domain and/or said Cat-domain by measurement of fluorescence by the donor, e.g., over time (e.g., one or more times before and one or more times after said incubation);

wherein the substance is identified as the inhibitor if fluorescence by the donor occurs at a lower level (e.g., a lower rate of increase) than that observed in the absence of said substance.

FRET donors and acceptors are well known in the art. Examples of donor/acceptor pairs include: fluorescein/tetramethylrhodamine; IAEDANS/fluorescein; EDANS/dabcyl; fluorescein/fluorescein; BODIPY FL/BODIPY FL; and fluorescein/QSY 7 and QSY 9 dyes (Invitrogen; Carlsbad, Calif.).

Often, the donor and acceptor dyes are different; in which case, FRET can be detected by the appearance of sensitized fluorescence of the acceptor or by quenching of donor fluorescence. When the donor and acceptor are the same, FRET can be detected by the resulting fluorescence depolarization. Nonfluorescent acceptors such as dabcyl and QSY dyes have the advantage of eliminating the potential problem of background fluorescence resulting from direct (i.e., nonsensitized) acceptor excitation.

An alternative assay format involves using an active PCSK9 Cat-domain to cleave an exogenously added peptide substrate corresponding to the Pro-domain cleavage site, or otherwise recognized by the PCSK9 Cat-domain active site.

For example, in an embodiment of the invention, such a peptide cleavage-based method would include the following steps:

(i) incubating a mixture comprising a peptide substrate with a PCSK9 Cat-domain wherein the peptide substrate is labeled with a FRET donor at one end and a FRET acceptor/fluorescence quencher at the other end; under conditions which allow proteolytic cleavage of the peptide within a defined cleavage site, in the presence of a substance to be tested for said inhibitor; and (ii) determining generation of cleavage products by measuring unquenched fluorescence caused by separation of labeled ends of the cleaved peptide, e.g., over time (e.g., one or more times before and one or more times after said incubation); wherein the substance is identified as the inhibitor if fluorescence resulting from this peptide cleavage occurs at a lower level (e.g., a lower rate of increase) than that observed in the absence of said substance.

In addition, the present invention provides an immobilized protein cleavage assay. Specifically, the assay comprises (i) immobilizing a protein comprising the Pro-Cat domain to a substrate, wherein autoproteolysis of the Pro-Cat polypeptide releases the Pro- or Cat-domain but retains the other domain on the substrate and (ii) detecting the domain released as a result of cleavage. For example, in an embodiment of the invention, the assay comprises:

(i) binding an (affinity tag)-Pro-Cat-(detectable label) or (detectable label)-Pro-Cat-(affinity tag) (e.g., FLAG-Pro-Cat-HisX6) protein to a substrate (e.g., beads such as sepharose or agarose) with affinity for the affinity tag;

(ii) incubating the bound protein under conditions that allow autoproteolysis of the ProCat polypeptide and release of the detectably labeled protein, in the presence of a substance to be tested for the PCSK9 inhibitor; and (iii) detecting the Cat-(detectable label) or (detectable label)-Pro protein which is released due to cleavage; wherein the substance is identified as an inhibitor if more Cat-(detectable label) or (detectable label)-Pro protein is detected associated with the substrate in the presence of the substance than in its absence; or if less of the Cat-(detectable label) or (detectable label)-Pro protein is detected liberated from the substrate.

The "affinity tag" should be capable of binding whatever substrate is selected for use in the assay. For example, HisX6 is generally compatible with $Ni^{2+}$ or $Co^{2+}$ containing substrates. "HisX6" is a 6 histidine tag. GST is generally compatible with glutathione containing substrates. The "detectable label" can be any acceptable label such as FLAG, myc or HA.

In an embodiment of the invention, the affinity tag bound substrate is assayed for the presence of Cat-(detectable label) or (detectable label)-Pro protein. In this embodiment of the invention, the substance is identified as an inhibitor if more Cat-(detectable label) or (detectable label)-Pro protein is detected associated with the substrate in the presence of the substance than in its absence. In an alternative embodiment of the invention, liberated Cat-(detectable label) or (detectable label)-Pro protein is detected, for example, in wash buffer which is used to remove cleaved protein from the protein which is still bound to the affinity substrate. In this embodiment, the substance is identified as an inhibitor if less liberated protein is in the wash in the presence of the substance than in its absence.

In an embodiment of the invention, the assay comprises:

(i) immobilizing an FLAG-Pro-Cat-HisX6 protein to a Nickel-substrate (e.g., beads conjugated to Nickel or a plate comprising immobilized Nickel);

(ii) incubating the bound protein under conditions that allow autoproteolysis of the ProCat polypeptide and release of the FLAG-Pro-moiety in the presence of a substance to be tested for the presence of a PCSK9 inhibitor;

(iii) contacting the immobilized protein with a denaturant (e.g., urea) to facilitate release of cleaved FLAG-Pro-polypeptide from the immobilized -Cat-HisX6 polypeptide and washing the cleaved polypeptide from the immobilized polypeptide; and (iv) determining the amount of FLAG-Pro-polypeptide which remains uncleaved and associated with the -Cat-HisX6 polypeptide; or determining the amount of FLAG-Pro-polypeptide which was cleaved and is associate with the denaturant wash; wherein the substance is identified as an inhibitor if more FLAG-Pro-associated with -Cat-HisX6 polypeptide (or associated with the affinity substrate) is detected in the presence of the substance than in its absence; or if less FLAG-Pro is detected in the wash in the presence of the substance than in its absence.

The PCSK9 inhibitors identified using any of the methods set forth herein may be used to treat various diseases, disorders and medical conditions. Accordingly, any of the methods for identifying inhibitors of PCSK9 may be used, for example, for identifying substances for reducing total cholesterol level, reducing low density lipoprotein cholesterol level, reducing apolipoprotein B level, reducing total cholesterol/high density lipoprotein ratio or reducing low density lipoprotein/high density lipoprotein ratio; and/or for treating or preventing hypercholesterolemia, treating or preventing hyperlipidemia, treating or preventing hypertriglyceridaemia, treating or preventing sitosterolemia, treating or preventing atherosclerosis, treating or preventing arteriosclerosis, treating or preventing coronary heart disease, treating or preventing vascular inflammation and/or treating or preventing xanthoma.

Any of the foregoing assays may be performed, optionally, in association with a positive-control or negative-control assay. For example, a positive-control assay may be performed in the presence of a substance known to be a PCSK9 inhibitor. The observation of inhibition of PCSK9 proteolysis in the assay confirms that the assay is functioning properly. Examples of known inhibitors include, for example, tosyl-L-lysine chloromethyl ketone (TLCK) or tosyl-L-phenylalanine chloromethyl ketone (TPCK). Such a positive-control method may comprise the following steps:

(i) incubating a mixture comprising a polypeptide comprising a PCSK9 Pro-Cat-domain under conditions which allow autoproteolytic cleavage of the polypeptide between the Pro-domain the Cat-domain in the presence of a positive-control substance known to inhibit PCSK9 proteolysis; and (ii) determining generation of said Pro-domain and/or said Cat-domain; wherein the assay is determined to be functioning properly if inhibition of PCSK9 proteolysis is observed, particularly, if more inhibition is observed than in the absence of the positive-control substance; e.g., in an negative-control assay.

For example, a negative-control assay may be performed in the presence of a substance known not to be a PCSK9 inhibitor (negative-control substance) (e.g., water or buffered water). The observation of little or no inhibition of PCSK9 proteolysis in the assay confirms that the assay is functioning properly. The negative-control assay will also reveal the maximum level of uninhibited proteolysis against which the level of proteolysis observed in the presence of a candidate substance may be compared. If the level of proteolysis in the presence of a candidate substance is lower than the maximum level observed in the negative-control assay, then the candidate may be considered a PCSK9 inhibitor. Such a negative-control method may comprise the following steps:

(i) incubating a mixture comprising a polypeptide comprising a PCSK9 Pro-Cat-domain under conditions which allow autoproteolytic cleavage of the polypeptide between the pro-domain the Cat-domain in the presence of a negative-control substance known not to inhibit PCSK9 proteolysis; and (ii) determining generation of said Pro-domain and said Cat-domain;

wherein the assay is determined to be functioning properly if no inhibition is observed and/or wherein the level of proteolysis observed is determined to be the maximum level of uninhibited PCSK9 proteolysis.

Similar positive and negative control assays may be adapted for use in conjunction with any of the assay formats discussed herein (e.g., HPLC or MALDI mass spectrometry)

EXAMPLES

The following information is provided for more clearly describing the present invention and should not be construed to limit the present invention. Any and all of the compositions and methods described below fall within the scope of the present invention.

Example 1

Cloning of PCSK9

Human PCSK9, corresponding to residues 31-454 (Pro-Cat-domains), was amplified to have CACC and the sequence for GS-(His)$_6$ at the 5'- and 3'-end respectively using the following primers:
Pro(+), 5'-CACCATGCAAGAGGATGAAGATGGAGAC-TATG-3'(SEQ ID NO: 5);
Cat(–), 5'-CTAATGATGGTGATGGTGGTGAGATC-CCTGCCAGCCTGCCCCGT-3'(SEQ ID NO: 6).

The PCR product was inserted into the pENTR/SD/D-TOPO vector (Invitrogen; Carlsbad, Calif.) according to the manufactures directions. The *E. coli* expression vector was created via the LR reaction with the pDest14 vector.
Human PCSK9 DNA Sequence Used for Cloning
ATGCAAGAGGATGAAGATGGAGACTAT-GAGGAGCTGGTCCTGGCTTTGCGATCT-GAAGAAGACGGACTGGCCGAGGC CCCAGAG-CATGGGACTACTGCGACCTTTCACAGGTGTGCAAA-AGACCCTTGGAGGCTGCCCGGGACTTACGTTGTGG TTCTGAAGGAAGAAACTCACTTGAGC-CAATCCGAACGAACAGCCCGGCGGTTG-CAAGCCCAGGCTGCGCGCCGCGGG TATTTGAC-TAAGATCCTTCATGTGTTCCATGGCCTGCTGCCAG-GGTTCCTGGTCAAGATGAGCGGGGATCTTCTCGA GCTGGCGCTGAAGCTGCCTCACGTAGAC-TATATCGAGGAAGATAGCTCTGTGT-TCGCTCAGAGCATCCCTTGGAACT TGGAGAGAAT-CACCCCCCCAGATATCGAGCTGACGAGTACCAAC-CACCGGACGGGGGCTCCCTGGTGGAAGTCTAC TTGCTGGACACCAGTATTCAGTCTGAC-CATAGGGAGATCGAGGGTCGGGTCATG-GTGACCGACTTTGAGAACGTCCC AGAAGAA-GACGGGACGAGATTTCACCGCCAGGCCAGTAAGT-GTGACTCACACGGAACGCATCTGGCTG-GTGTTGTCA GTGGGAGGGACGCAGGTGTG-GCTAAGGGCGCCAGCATGCGCAGCCT-GAGAGTGCTCAATTGCCAGGGGAAGGGGACC GTGAGTGGAACTCTGATTGGACTGGAGT-TCATTAGGAAGAGCCAGCTGGTGCAGC-CGGTGGGCCCCTTGGTGGTATT GCTGCCCCTG-GCAGGAGGGTATAGCCGGGTGCTTAATGCCGCCTG-TCAGAGGCTGGCCAGAGCCGGCGTTGTTCTGG TGACTGCCGCCGGAAATTTCCGGGAC-GATGCTTGCTTGTACAGCCCAGC-GAGCGCTCCGGAAGTGATCACAGTAGGC GCAAC-GAACGCCCAGGATCAGCCTGTAACCCTGGGGACT-CTGGGAACCAACTTTGGACGGTGTGTC-GATCTTTTTGC TCCCGGAGAGGATATTATCGGAG-CATCCTCAGATTGTTCCACCTGCTTTG-TATCCCAGAGCGGAACCTCTCAGGCAG CTGCACACGTTGCTGGAATTGCCGCTAT-GATGTTGTCTGCCGAGCCGGAGCTCA-CATTGGCCGAGCTGAGACAGCGC TTGATTCACT-TCAGCGCGAAAGATGTGATAAATGAGGCCTGGTT-TCCAGAGGACCAACGAGTTCTGACCCCCAACCT GGTGGCTGCACTGCCACCTTCTAC-CCACGGGGCAGGCTGGCAG (SEQ ID NO: 7; encoding human PCSK9 amino acids 31-454)
Amino Acid Sequence of Mature PCSK9 Propeptide
MQEDEDGDYEELVLALRSEEDGLAEAPE-HGTTATFHRCAKDPWRLPGTYVVVL-KEETHLSQSERTARRLQAQAARRG YLTKILHVFH-GLLPGFLVKMSGDLLELALKLPHVDYIEEDSSVFAQ (SEQ ID NO: 8; encoding human PCSK9 amino acids 31-152 (Methionine #1 added))
Catalytic Domain
SIPWNLERITPPRYRADEYQPP-DGGSLVEVYLLDTSIQSDHREIEGRVM-VTDFENVPEEDGTRFHRQASKCDSHGTH LAGVVS-GRDAGVAKGASMRSLRVLNCQGKGTVSGTLIGLEFI-RKSQLVQPVGPLVVLLPLAGGYSRVLNAACQRLAR AGVVLVTAAGNFRDDACLYSPASAPE-VITVGATNAQDQPVTLGTLGTNF-GRCVDLFAPGEDIIGASSDCSTCFVSQS GTSQAAAH-VAGIAAMMLSAEPELTLAELRQRLIHFSAKDVINEA-WFPEDQRVLTPNLVAALPPSTHGAGWQGSHHHH HH (Seq Id No: 9; Encoding Human Pcsk9 Amino Acids 153-454)
Pro-Cat-Domain Polypeptide
QEDEDGDYEELVLALRSEEDGLAEAPEH-GTTATFHRCAKDPWRLPGTYVVVL-KEETHLSQSERTARRLQAQAARRGY LTKILHVFH-GLLPGFLVKMSGDLLELALKLPHVDYIEEDSSVFAQ-SIPWNLERITPPRYRADEYQPPDGGSLVEVYL LDT- SIQSDHREIEGRVMVTDFENVPEEDGTR-
FHRQASKCDSHGTHLAGVVSGRDAGVAK-
GASMRSLRVLNCQGKGTV
SGTLIGLEFIRKSQLVQPVGPLVVLL-
PLAGGYSRVLNAACQRLARAGVV-
LVTAAGNFRDDACLYSPASAPEVITVGA
TNAQDQPVTLGTLGTNFGRCVDLFAPGE-
DIIGASSDCSTCFVSQSGTSQAAAHVA-
GIAAMMLSAEPELTLAELRQRL IHFSAKDVINEAWF-
PEDQRVLTPNLVAALPPSTHGAGWQGSHHHHHH
(SEQ ID NO: 10)

Example 2

Expression and Purification of PCSK9 Expression

A 150 ml volume of Terrific Broth+150 µg/ml carbenicillin was inoculated with a colony of BL-21(DE3) cells, which had been transformed with the pPCSK9-454 plasmid and grown on LB agar+100 µg/ml carbenicillin. The 150 ml culture was incubated at 37° C. in a 500 ml baffled flask at 300 rpm. When it reached an $OD_{600}$ of 0.9, the culture was placed on ice, then stored overnight at 4° C. Ten two liter flasks, each containing a liter of terrific broth+150 µg/ml carbenicillin, were each inoculated with 10 ml of the 150 ml culture, and incubated at 37° C. at 300 rpm, until they reached an $OD_{600}$ of 1.3. The 10 liters of culture were used to inoculate a 100 liter tank of terrific broth+100 µg/ml carbenicillin, which was incubated at 37° C. until it reached an $OD_{600}$ of 0.8. The temperature was then reduced to 16° C. and the cells induced overnight at this temperature with 0.5 mM IPTG. The cells were harvested by centrifugation and the cell pellets stored at −80° C.

Cell pellets from 20 liters of the 100 liter induction were extracted in 1500 ml of 50 mM sodium phosphate, pH 7.9, 0.3 M NaCl, by 5 passes through an OmiMixer probe and 2 passes through a Microfluidizer. All extraction and purification was performed on ice or at 4° C.

The lysed cells were centrifuged at 215,000×g for 40 minutes, and the supernatant was mixed, end over end, with 7 ml of Ni-NTA Superflow agarose (Qiagen; Valencia, Calif.) for 30 minutes. The Ni-NTA agarose was then packed in a column, washed with 70 ml of 50 mM sodium Hepes, pH 7.5, 1.0 M NaCl, 10% glycerol and 25 mM imidazole, and 70 ml of 50 mM sodium Hepes, pH 7.5, 0.3 M NaCl, 10% glycerol and 50 mM imidazole. The PCSK9 was eluted with 50 mM sodium Hepes, pH 7.9, 0.3 M NaCl, 10% glycerol and 400 mM imidazole.

The PCSK9 containing fractions were pooled, 0.2 micron filtered and applied to a 2.6×60 cm Superdex 75 column (GE Healthcare; Piscataway, N.J.) equilibrated with 25 mM sodium Hepes, pH 7.5, 1 mM EDTA, 0.15 M NaCl and 10% glycerol. The PCSK9 containing fractions were pooled, concentrated to 1.2 mg/ml on an Amicon YM 10 membrane, centrifuged at 98,000×g for 20 minutes and the supernatant aliquots flash frozen in liquid nitrogen. Yields: 0.5 mgs/liter that is ~95% pure.

Example 3

Assays for PCSK9 Cis-Cleavage

This example, demonstrates use of the PCSK9 protease assays of the present invention in various formats.

Assay Example 1

High Throughput Screening Using High Throughput Chromatography

Unprocessed PCSK9 (18 µM for NanoStream experiment, 8 µM for BioRad Experion experiment) was incubated at 25° C. in 25 mM Hepes pH 7.5, 150 mM NaCl, 10% glycerol and 1 mM EDTA (4% DMSO may be added to uninhibited control assays when run in conjunction with assays that include inhibitors dissolved in DMSO). At the designated time points (t=0 minutes, 60 minutes and 240 minutes), aliquots from the 18 µM incubation were quenched by adding guanidine hydrochloride to a concentration of 6M, then the quenched reaction was applied (1 µl) to NanoStream Brio #4207007 (300 Å, C4) chromatography cassette. Following gradient elution, from the cassette, using 0.1% TFA in water (solvent A) and 0.085% TFA in acetonitrile (solvent B), the peaks were quantitated by absorbance at 214 nm. These data are set forth in FIG. 2 (panel A).

In addition, a time course of propCSK9 processing (fraction propCSK9/total PCSK9) using high throughput NanoStream LD and BioRad Experion Automated Electrophoresis station and the data from the analyses were plotted side-by-side. These data are set forth in FIG. 2 (panel B).

Figure 2A:
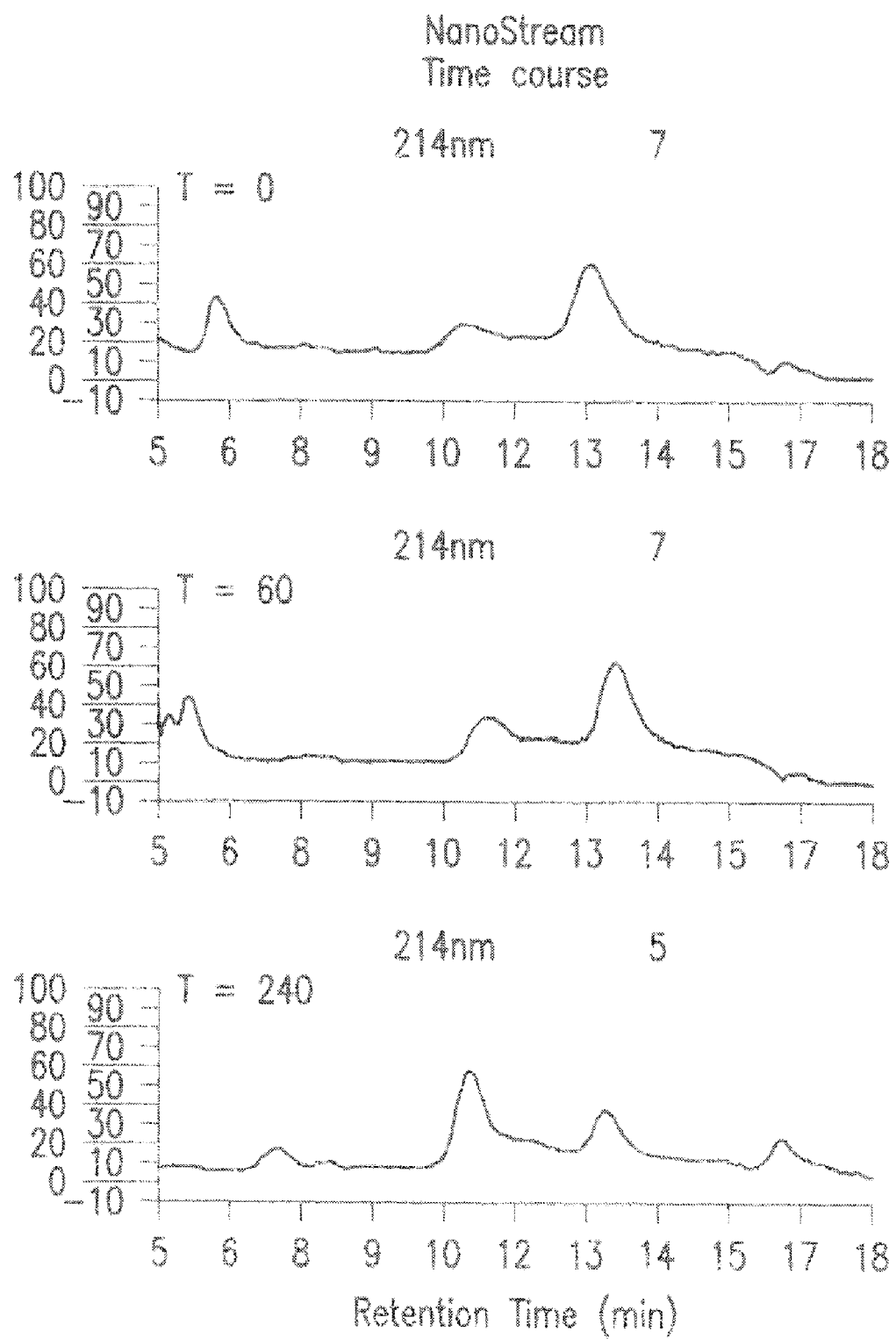
FIG. 2: High throughput liquid chromatography analysis of PCSK9 autoproteolysis assay. Panel A: Analysis of time course of PCSK9 processing assay quenched at time points t=0 minutes, t=60 minutes and t=240 minutes on Nanostream Brio high throughput liquid chromatography system. The peak, with a retention time of approximately 13 minutes corresponds to ProCat polypeptide whereas the peak, at approximately 11 minutes, corresponds to Cat-domain. Panel B: Time course of propCSK9 processing (fraction propCSK9/Total PCSK9) using high throughput NanoStream LD (large circles) or BioRad Experion Automated Electrophoresis station (small circles).
Figure 2B:
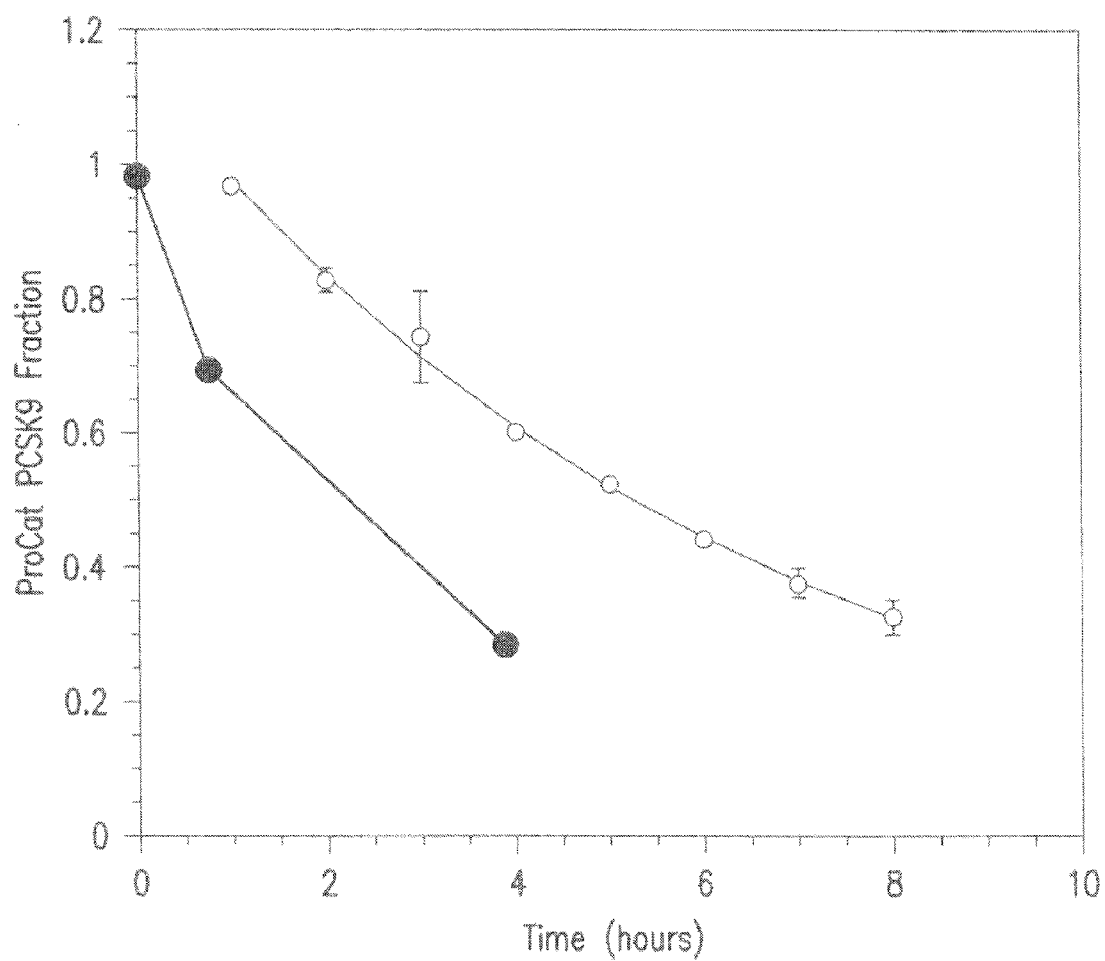

FIG. 2 shows that a non-optimized high throughput chromatography system (NanoStream) can detect conversion of substrate to product with similar kinetics to the low throughput electrophoresis system (BioRad Experion Automated Electrophoresis station).

Figure 5A:
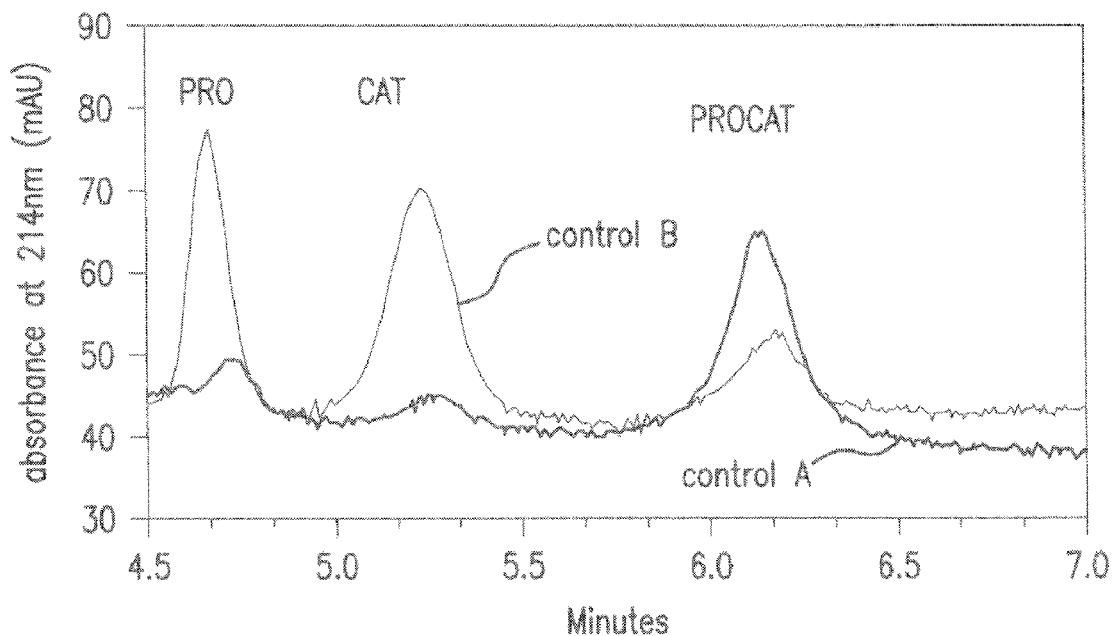
FIG. 5(a)-(b): Cis-cleavage inhibition of unprocessed PCSK9 by TLCK.

Furthermore, a chromatographic analysis of PCSK9 autoproteolysis was performed in the presence of various inhibitors. This assay was used to determine the effect of the inhibitors Tris (2-carboxyethyl) phosphine (TCEP; a reducing agent) and tosyl-L-lysine chloromethyl ketone (TLCK) on the PCSK9 autoproteolysis reaction. The data generated in these assays are set forth in FIG. 5. In these assay, the ProCat peak is uncleaved PCSK9 whereas the Pro- and Cat-peaks indicate generation of the Pro- and Cat-domains, which indicates autoproteolytic cleavage by PCSK9. FIG. 5(a) sets forth the data in the assay wherein the Tris (2-carboxyethyl) phosphine inhibitor was assayed. In the control-A experiment (data represented by control-A curve in FIG. 5(a)), complete inhibition of cis-cleavage activity by addition of 5 mM Tris (2-carboxyethyl) phosphine was observed. In the control-A experiment, Tris (2-carboxyethyl) phosphine was added at t=zero minutes of a 6 hour incubation. Tris (2-carboxyethyl) phosphine is a disulfide reducing agent that is not oxidized by air.

In the control-B experiment set forth in FIG. 5(a), Tris (2-carboxyethyl) phosphine was added at the end of a 6 hour incubation. The appearance of the Pro- and Cat-domains in the control B assay indicate the occurrence of autoproteolysis.

Figure 5B:
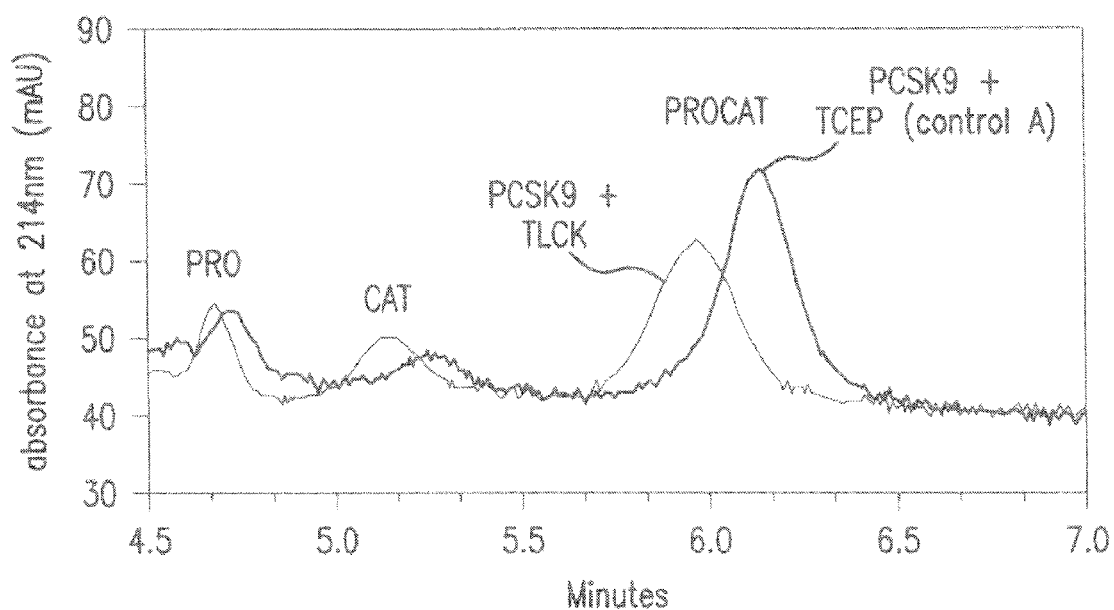

FIG. 5(b) sets forth data wherein inhibition mediated by TCEP (Tris (2-carboxyethyl) phosphine) and TLCK (tosyl-L-lysine chloromethyl ketone) are compared, side-by-side, in an autoproteolysis assay. The TLCK-treated sample showed a small decrease in the ProCat peak (Uncleaved PCSK9) and a slight increase in Pro- and Cat-domains in comparison to Control-A (assay performed with TCEP). The inhibitors are added at time zero. TCEP was added at 5 mM to quench the reaction; this sample serves as the 100% inhibited control—Control A in FIG. 5. TLCK was added at a concentration of 77 µM.

Assay Example 2

High Throughput Screening Using High Throughput HPLC

Figure 3:
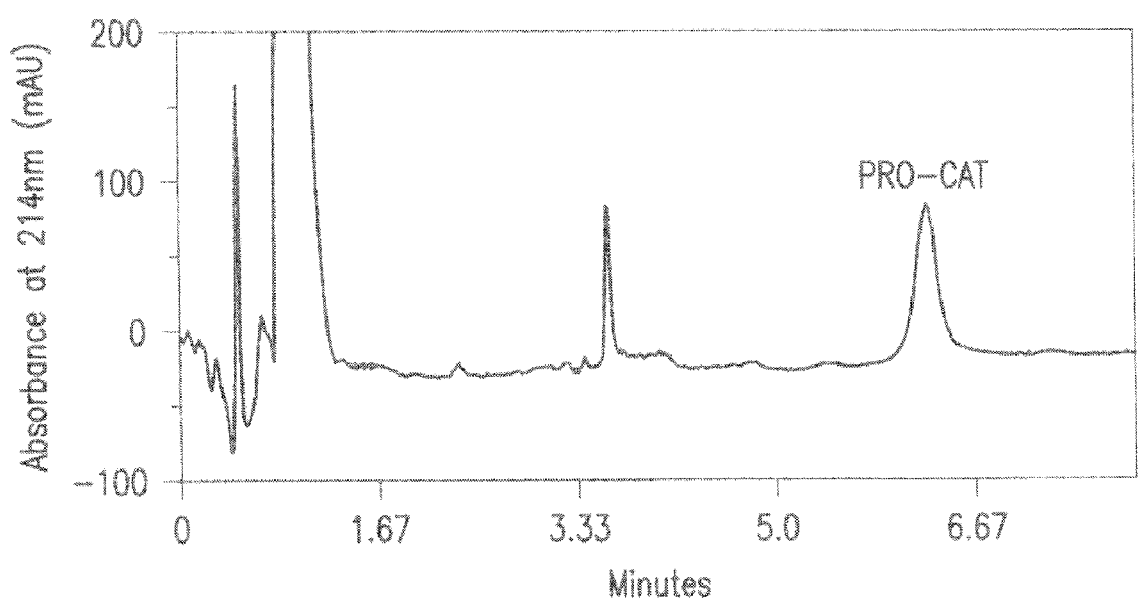
FIG. 3: HPLC chromatogram of unprocessed PCSK9.

An HPLC (high pressure liquid chromatography) method was developed for separation and quantitation of the Pro-Catdomain (intact protein) and individual Pro- and Cat-domains of PCSK9. The samples used were:

An HPLC analysis was performed on unprocessed PCSK9. A sample containing 12 uM unprocessed PCSK9 in 25 mM Hepes buffer pH 7.5, 150 mM NaCl, 1 mM EDTA, 10% glycerol and 4.0% DMSO was incubated at 25° C. The cis-cleavage reaction was quenched at zero minutes by addition of TCEP (Tris (2-carboxyethyl) phosphine hydrochloride) (5 mM), a reducing agent, and guanidine HCl (2.5M). One microliter of the reaction mixture was analyzed directly by reversed phase-HPLC using Express-LC100, a micro fluidic chromatographic system from Eksigent. The separations were carried out using a C4 column (0.3×150 mm packed with 3 micron silica particles with average pore size of 300 Å). The sample components were separated by gradient elution using 0.1% TFA in water (solvent A) and 0.1% TFA in acetonitrile (solvent B)). The flow rate was 12 ul per minute and the sample components were detected at 214 nm. The amount of ProCat polypeptide was calculated as % of sum of peak areas corresponding to Pro-, Cat- and ProCat domains. The chromatogram revealed a large peak for ProCat and trace amounts for Pro- and Cat-. The data from the HPLC analysis of unprocessed PCSK9 is shown in FIG. 3.

Figure 4:
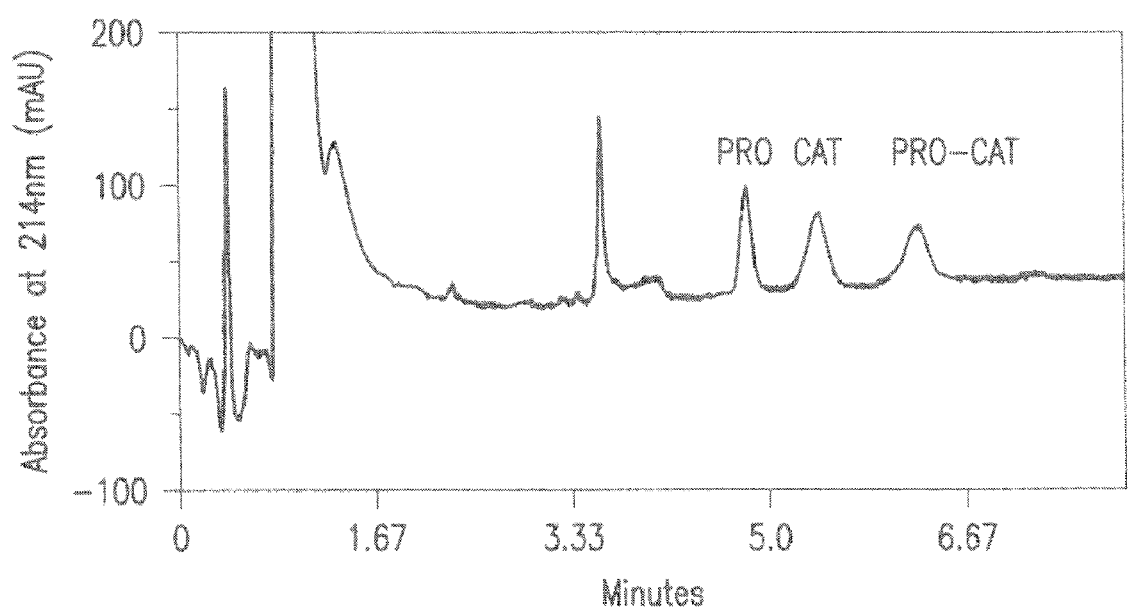
FIG. 4: HPLC chromatogram of PCSK9 after cis-cleavage.

An HPLC analysis of cis-cleaved PCSK9 was also performed. A sample containing 12 uM unprocessed PCSK9 in 25 mM Hepes buffer pH 7.5, 150 mM NaCl, 1 mM EDTA, 10% glycerol and 4.0% DMSO was incubated at 25° C. The cis-cleavage reaction was quenched after 6 hours by addition of 5 mM TCEP and 2.5 mM of guanidine HCl. Cis-cleavage produced significant amounts of Pro- and Cat-polypeptides with simultaneous reduction in ProCat polypeptides at the end of 6 hours of incubation. The data from the HPLC analysis of processed PCSK9 is shown in FIG. 4. The peaks corresponding to Pro-, Cat- and ProCat polypeptides are labeled.

HPLC analysis of PCSK9 incubated in the presence of inhibitor was also performed. Sample containing 12 uM unprocessed PCSK9 in 25 mM Hepes buffer pH 7.5, 150 mM NaCl, 1 mM EDTA, 10% glycerol and 4.0% DMSO were incubated at 25° C. Unprocessed PCSK9 was quenched at zero minute (Control A: complete inhibition of cis-cleavage) and after 6 hours (Control B: maximum cleavage) by addition of 5 mM TCEP and 2.5 mM of Guanidine HCl. Peak area calculations indicated that % of ProCat was cleaved into Pro- and Cat-domains after 6 hours. Cis-cleavage resulted in significant reduction of ProCat with concomitant increase in Pro- and Cat-. The data from this experiment are set forth in the top panel of FIG. 5.

Unprocessed PCSK9 was quenched at zero minute (Control A) and incubated at 25° C. with 77 uM TLCK (PCSK9+TLCK) for 6 hours and subsequently quenched as above. In the presence of 77 uM TLCK significant amount of ProCat remained uncleaved at the end of 6 hour incubation suggesting significant inhibition of cis-cleavage reaction. The data from this experiment are set forth in the bottom panel of FIG. 5.

Assay Example 3

Method for PCSK9 MALDI Cis Cleavage Assay

A mass spectrometry (Matrix Assisted Laser Desorption Ionization Mass Spectrometry; MALDI-MS) method was developed for the separation and ratiometric comparison of the ProCat-domain (intact protein) and individual Pro- and Cat-domains of PCSK9. MALDI-MS is a hard ionization technique that permits mass/charge measurements from 300 to greater than 150,000 Daltons and quantitation of intensity for a given m/z signal. While correlation of signal intensity to absolute amounts is inaccurate, intra-sample ratios are possible assuming ionization of each signal component is constant between samples. In the case of PCSK9 cis-cleavage, this permits intensity ratio measurements from signal arising from Pro-, Cat- and ProCat polypeptides within a given sample to estimate percent PCSK9 processed.

Samples included 5 pmol PCSK9 unprocessed in 10 µL 50 mM phosphate, 150 mM NaCl, 2.5% DMSO+/−inhibitor (5-80 micromolar, depending on solubility, of inhibitor). Upon thawing of PCSK9 stock stored in −80° C., protein was immediately diluted in assay buffer and combined with inhibitor to initiate the test. For single point values, the test duration spanned 4-6 hours (depending on enzyme activity and temperature) after which the sample was quenched with Tris(2-Carboxyethyl)-Phosphine Hydrochloride (TCEP) to a final concentration of 50 mM. This was followed by 10 µL of 10% acetonitrile, 89.5% HPLC grade water, 0.5% formic acid "Equilibration Solution". Samples were immediately frozen until further processing.

In preparation for MALDI analysis, a mixture of saturated sinapic acid in 50% acetonitrile, 49.5% HPLC grade water, 0.5% formic acid was mixed at room temperature. Particulates were pelleted by 1 minute of centrifugation. This solution was kept for 48 hours and then discarded. 1 µL of this material was deposited in each well of a 96 well assay plate (Nunc) "Elution Plate" and allowed to dry prior to receiving Zip Tip eluates. C4 Zip Tips (Millipore Catalog ZTC04S096) were wetted using 90% acetonitrile, 9.5% HPLC grade water, 0.5% formic acid "Wash Solution". Zip Tip treatment may be performed using a single channel or multi-channel pipettor. This was followed by equilibration first in 60% acetonitrile, 39.5% HPLC grade water, 0.5% formic acid "Elution Solution", then in Equilibration Solution by repeated pipetting. Sample was applied to the Zip Tips by means of 8 aspirating and dispensing maneuvers after which the loaded Zip Tips were washed 2 times using Equilibration Solution and 1 time using 30% acetonitrile, 69.5% HPLC grade water, 0.5% formic acid. Polypeptides were eluted with 5 µL Elution Solution into wells of the Elution Plate with sinapic acid matrix present. Elution Solution was aspirated and dispensed 3 times for maximum recovery. Volume reduction through evaporation, under ambient conditions, occurred over the course of 5 to 8 minutes for eluates present in the Elution Plate. Eluates were not allowed to evaporate to dryness. 1 µL of the concentrated eluate+sinapic acid matrix mix was then applied to the MALDI target and evaporation of the sample occurred in ambient conditions.

The hardware used was a Shimazdu CFR+ with a 384 well steel target (part DE-1580TA) operating Kratos Software Version 2.4.1. Data acquisition was automated using preset conditions recorded in a method with raster laser shot patterns changing between data sets. All signal was captured (as opposed to optimized) and exported as a text file with mass and intensity values typically resolved to 0.3 amu. In-house drafted software processed the data files by first smoothing the data using a Moving Average using 100 datapoints, then identifying the m/z values corresponding to the masses of interest, including the $[M+2H]^{2+}$ values for both ProCat and Cat-polypeptides, but not Pro-. The program drew a baseline based on standard peak detection algorithms and calculated the background subtracted peak area. Peak areas were stored in a results file and chromatograms were exported for visual inspection. Peak areas were imported into a spreadsheet program where ratios were determined using the following equation:

Fraction ProCat=(ProCat$[M+H]^+$+ProCat$[M+2H]^{2+}$)/ (ProCat$[M+H]^+$+ProCat$[M+2H]^{2+}$+Cat$[M+H]^+$+ Cat$[M+2H]^{2+}$+Pro$[M+H]^+$)

Dynamic range was defined as the Fraction ProCat (TCEP treated)−Fraction ProCat (no treatment)

Percent inhibition by a potential inhibitor was defined as (Fraction ProCat (inhibitor treated)−Fraction ProCat (no treatment))×100.

Figure 6A:
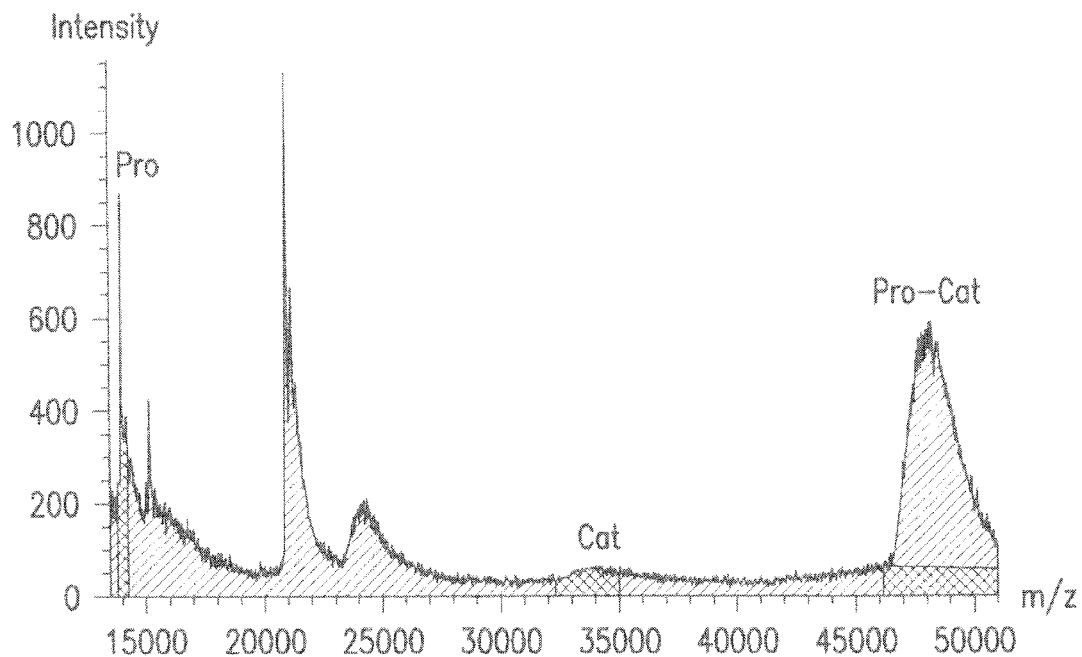
FIG. 6: MALDI mass spectrometry spectrum for PCSK9 autoproteolysis assay. (a) analysis of assay wherein no cleavage occurred. TCEP was added before incubation; (b) analysis of assay wherein cleavage was allowed to proceed for 6 hours in the absence of protease inhibitor. In each, the peaks corresponding to the Cat-domain and ProCat peptide are labeled.
Figure 6B:
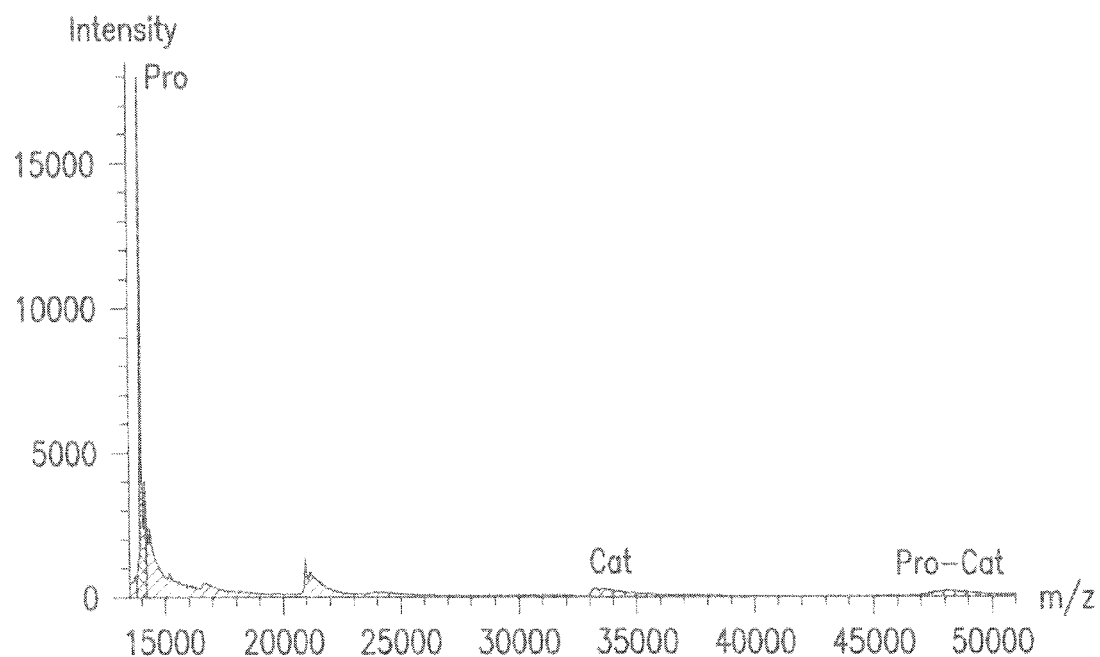

The data generated in this assay are set forth in FIG. 6. This assay detected all three components of PCSK9 cis-cleavage reaction (Pro-Cat polypeptide, Pro-domain and Cat-domain) by MALDI mass spectrometry. The spectrum illustrated an excellent S/N ratio for the components of interest.

Assay Example 4

SDS PAGE Cis-Cleavage Assay

Forty microliter aliquots of 8.4 µM unprocessed PCSK9 (9-454) were incubated at 25° C. after adding 1.6 µl of DMSO or 1.6 µl of 2 mM compound in DMSO. Final incubation conditions: 25 mM sodium Hepes, pH 7.5, 0.15 M NaCl, 1 mM EDTA, 10% glycerol and 4% DMSO.

The activity was quenched by adding one volume of NuPAGE® LDS Buffer (Invitrogen) to each sample after the indicated incubation time, and heating at 100° C. for 5 minutes. The unprocessed PCSK9 sample was quenched immediately after adding the DMSO.

Five micrograms of each sample were loaded on 12% NuPAGE® Bis-Tris gels, and electrophoresed under reducing conditions at 200 V in NuPAGE® MOPS SDS Running buffer.

The data from these assays is shown in FIG. 1. Sample number: 1, unprocessed PCSK9; 2, PCSK9 processed for 23 hours; 3, PCSK9 processed for 6 hours; and 4, PCSK9 processed for 6 hours with 77 µM PCSK9 inhibitory compound.

Assay Example 5

Cis-Cleavage Assay for PCSK9 Using Immuno-Detection Methods

This example describes an assay to monitor the cis-cleavage of human PCSK9 using immuno-detection methods. A construct of human PCSK9 was created to have an N-terminal FLAG-tag and a $(His)_6$-tag on the C-terminus. After incubation, the reaction was quenched and the domains were disassociated with 4.0 M urea. The protein was transferred to and bound, via the His-tag, to a HisSorb plate (Qiagen; Valencia, Calif.; nickel-nitrilotriacetic acid (Ni-NTA) coated plate). The amount of cleavage was determined by measuring the remaining FLAG-tag using standard ELISA techniques. Using this method, the sensitivity of the assay was increased at least 1000-fold over gel-based techniques and the microtiter format makes the assay compatible with high throughput screening methods.

Cloning and expression. A DNA fragment corresponding to residues 31-454 of human PCSK9 (Pro-Cat domains) was made synthetically (GeneScript Corp., Piscataway, N.J.). Additional bases were included to add a Not1 restriction site and a Shine-Dalgarno initiation sequence to the 5'-end. A GS-$(His)_6$ tag followed by a Asc1 restriction site was added to the 3'-end. A Gateway vector of PCSK9 was produced as FLAG-Pro-Cat(454)-GS-$(His)_6$ by restriction digestion/ligation into the pDest14 expression vector. Expression and purification of the protein was done as previously described with aliquots frozen at −80° C.

Figure 7:
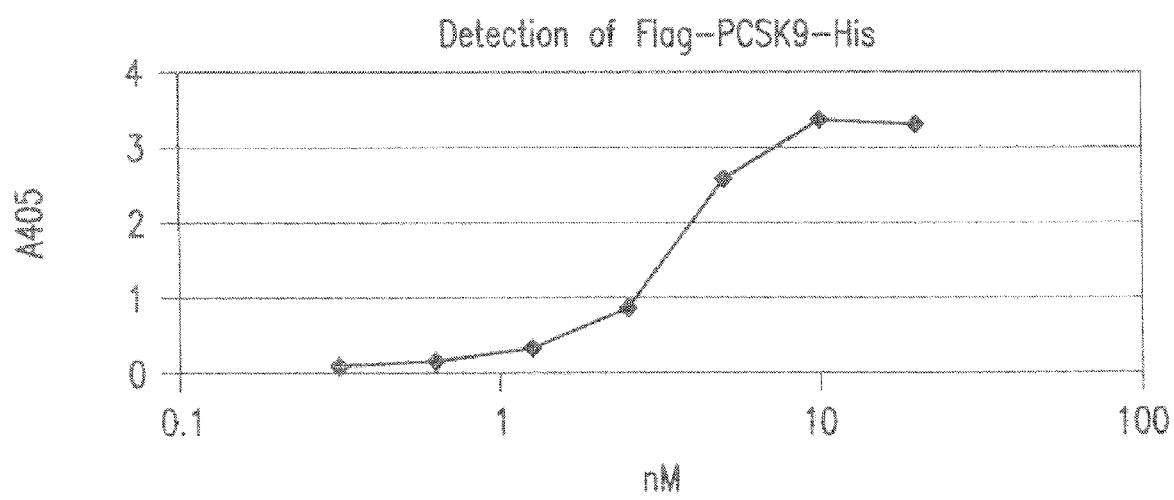
FIG. 7: Immunodetection of FLAG-PCSK9-HisX6 by ELISA to evaluate assay sensitivity. Quantity of FLAG-PCSK9-HisX6 observed to be associated with the Hisorb plate, as a function of A405, at various concentrations of protein (nM).

Assay protocol-Sensitivity of ELISA method. PCSK9 was defrosted and diluted to 20 nM in assay buffer (25 mM Tris-HCl, 0.15M NaCl, 0.2% BSA). Serial dilutions were made and the diluted protein was transferred to a 96-well HisSorb plate. After binding for 1 hour at room temperature, the plate was incubated with primary antibody (Anti-FLAG MAb, 0.4 ug/ml, Sigma F1804) for 1 hour followed by incubation with second antibody (Goat anti mouse-PEROX 1-2500). Detection was done at $A_{405nm}$ after development with ABTS substrate. Inhibition assays were typically done at 2.5-5 nM protein concentration (FIG. 7).

Figure 8:
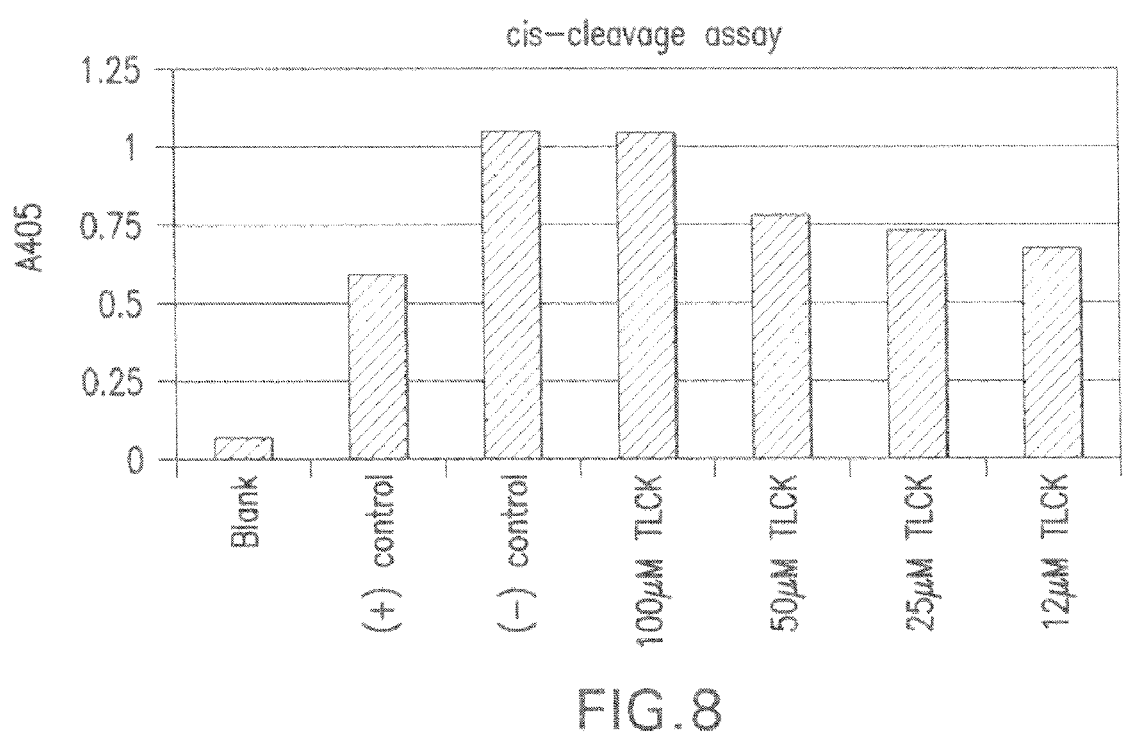
FIG. 8: Inhibition of PCSK9 with TLCK in immunodetection assay. Quantity of FLAG-PCSK9-HisX6 observed to be associated with the Hisorb plate, as a function of A405, at various concentrations of TLCK inhibitor.
Figure 9:
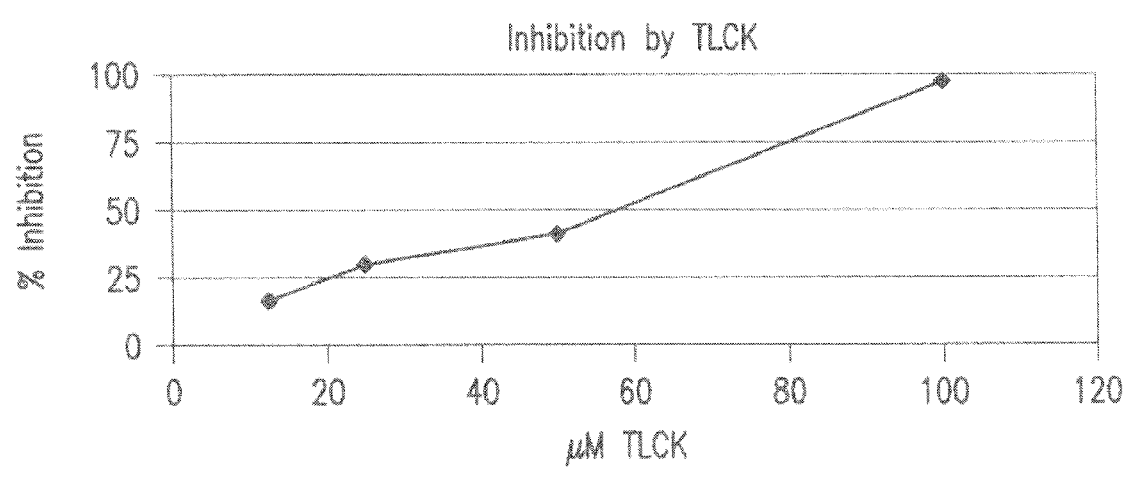
FIG. 9: Inhibition of PCSK9 with TLCK in immunodetection assay. Percentage of PCSK9 proteolysis inhibition at various concentrations of TLCK inhibitor.

Assay protocol-Inhibition of cis-cleavage. 100 ul aliquots of freshly diluted PCSK9 were delivered into wells of a 96-well polypropylene assay plate. Two microliters of inhibitor or DMSO were added to each well and the plate was incubated at 30° C. for 4 hours. An equal volume of 8M urea was added and the solution was transferred to a HisSorb plate. After binding for 1 hour, the wells are washed 2× with 25 mM Tris-HCl pH 8.0, 0.15 M NaCl to remove the urea. Immuno-detection of the remaining FLAG epitope was done as described above. The positive control (0% inhibition) was measured in the presence of 2% DMSO. The negative control (100% inhibition) was measured in the presence of 100 uM TLCK or 4M urea. Results of a typical experiment are shown in FIGS. 8 and 9. FIG. 8 shows the raw data and FIG. 9 data was converted % inhibition units.

DNA sequence of Flag-Pro-Cat(454)-GS-$(His)_6$ used for immuno-cis cleavage assay: GCGGCCGCCTTGTT-TAACTTTAAGAAGGAGCCCTTCACCATG-GATTATAAGGACGACGATGATAAGCAAGAGGATGA AGATGGAGACTATGAGGAGCTGGTCCTG-GCTTTGCGATCTGAAGAAGACGGACTG-GCCGAGGCCCCAGAGCATGGGA CTACTGCGAC-CTTTCACAGGTGTGCAAAAGACCCTTGGAGGCTG-CCCGGGACTTACGTTGTGGTTCTGAAGGAAGAA ACTCACTTGAGCCAATCCGAACGAA-CAGCCCGGCGGTTGCAAGCCCAGGCT-GCGCGCCGCGGGTATTTGACTAAGAT CCTTCATGT-GTTCCATGGCCTGCTGCCAGGGTTCCTGGTCAAGA-TGAGCGGGGATCTTCTCGAGCTGGCGCTGAAGC TGCCTCACGTAGACTATATCGAGGAA-GATAGCTCTGTGTTCGCTCAGAGCATC-CCTTGGAACTTGGAGAGAATCACC CCCCCCA-GATATCGAGCTGACGAGTACCAACCACCGGACGG-GGGCTCCCTGGTGGAAGTCTACTTGCTG-GACACCAG TATTCAGTCTGACCATAGGGAGATC-GAGGGTCGGGTCATGGTGAC-CGACTTTGAGAACGTCCCAGAAGAAGACGGGA CGAGATTTCACCGCCAGGCCAGTAAGT-GTGACTCACACGGAACGCATCTGGCTG-GTGTTGTCAGTGGGAGGGACGCA GGTGTG-GCTAAGGGCCCAGCATGCGCAGCCTGAGAGTGC-TCAATTGCCAGGGGAAGGGGACCGT-GAGTGGAACTCT GATTGGACTGGAGTTCATTAG-GAAGAGCCAGCTGGTGCAGCCGGTGGGC-CCCTTGGTGGTATTGCTGCCCCTGGCAG GAGGGTATAGCCGGGTGCTTAATGCCGC-CTGTCAGAGGCTGGCCAGAGCCGGCGT-TGTTCTGGTGACTGCCGCCGGA AATTTCCGGGAC-GATGCTTGCTTGTACAGCCCAGCGAGCGCTCCGGA-AGTGATCACAGTAGGCGCAACGAACGCCCA GGAT-CAGCCTGTAACCCTGGGGACTCTGGGAACCAACTT TGGACGGTGTGTCGATCTTTTTGCTC-CCGGAGAGGATATTATCGGAGCATCCT-CAGATTGTTCCACCTGCTTTGTAT CCCAGAGCG-GAACCTCTCAGGCAGCTGCACACGTTGCTGGAATT-GCCGCTATGATGTTGTCTGCCGAGCCGGAGCTC ACATTGGCCGAGCTGAGACAGCGCT-TGATTCACTTCAGCGCGAAAGATGT-GATAAATGAGGCCTGGTTTCCAGAGGA CCAAC-GAGTTCTGACCCCCAACCTGGTGGCTGCACTGCC-ACCTTCTACCCACGGGGCAGGCTG-GCAGGGATCTCACC ACCATCACCATCATT-AGGGCGCGCC (SEQ ID NO: 11) (Includes the restriction sites as well as the Shine-Dalgarno initiation sequence at the 5'-end)

Amino acid sequence of the Flag-Propeptide (Flag epitope underscored): <u>MDYKDDDDK</u>QEDEDGDYEELVLALRSEEDGLAEAPEHGTTATFHRCAKDPWRLPGTYVVVLKEETHLSQSERTARRLQAQAARRGYLTKILHVFHGLLPGFLVKMSGDLLELALKLPHVDYIEEDSSVFAQ (SEQ ID NO: 12)

Amino acid sequence of the catalytic domain (GS linker and His-tag underscored): SIPWNLERITPPRYRADEYQPPDGGSLVEVYLLDTSIQSDHREIEGRVMVTDFENVPEEDGTRFHRQASKCDSHGTH LAGVVSGRDAGVAKGASMRSLRVLNCQGKGTVSGTLIGLEFIRKSQLVQPVGPLVVLLPLAGGYSRVLNAACQRLARAGVVLVTAAGNFRDDACLYSPASAPEVITVGATNAQDQPVTLGTLGTNFGRCVDLFAPGEDIIGASSDCSTCFVSQS GTSQAAAHVAGIAAMMLSAEPELTLAELRQRLIHFSAKDVINEAWFPEDQRVLTPNLVAALPPSTHGAGWQ<u>GSHHHHHH</u> (SEQ ID NO: 13)

The present invention is not to be limited in scope by the specific embodiments described herein. Indeed, the scope of the present invention includes embodiments specifically set forth herein and other embodiments not specifically set forth herein; the embodiments specifically set forth herein are not necessarily intended to be exhaustive. Various modifications of the invention in addition to those described herein will become apparent to those skilled in the art from the foregoing description. Such modifications are intended to fall within the scope of the claims.

Patents, patent applications, publications, product descriptions, and protocols are cited throughout this application, the disclosures of which are incorporated herein by reference in their entireties for all purposes.

We claim:

1. A method for identifying an inhibitor of proprotein convertase subtilisin kexin type 9 (PCSK9) comprising: incubating a mixture comprising a polypeptide comprising a PCSK9 ProCat-domain under conditions which allow autoproteolytic cleavage of the polypeptide between the Pro-domain and the Cat-domain in the presence of a substance to be tested for inhibition; and determining generation of said Pro-domain or said Cat-domain, or both, wherein the substance is identified as the inhibitor if said generation of said domain(s) occur(s) at a lower level than that observed in the absence of said substance.

2. The method of claim 1 wherein said Pro-domain or Cat-domain or both are determined by chromatographically separating the polypeptides in said mixture and analyzing said separated polypeptides to determine said domain(s).

3. The method of claim 1 wherein said Pro-domain or Cat-domain or both are determined by mass spectroscopically analyzing the polypeptides in said mixture to determine said domain(s).

4. The method of claim 1 wherein said Pro-domain or Cat-domain or both are determined by matrix-assisted laser desorption/ionization mass spectrometrically analyzing the polypeptides in said mixture to determine said domain(s).

5. The method of claim 2 wherein the mixture is chromatographically separated over a hydrophobic interaction substrate.

6. The method of claim 2 wherein the mixture is separated using a high pressure liquid chromatography system.

7. The method of claim 2 wherein eluate from said chromatographic separation is analyzed spectrophotometrically wherein absorbance of light at 214 nm wavelength is measured.

8. The method of claim 1 wherein said Pro-domain or Cat-domain or both is determined by performing SDS-PAGE analysis of polypeptides in said mixture.

9. The method of claim 1 wherein said Pro-domain or Cat-domain or both is determined by performing SDS microchip electrophoresis of said mixture.

10. The method of claim 1 comprising
 (i) binding a PCSK9 Pro-Cat polypeptide to an affinity resin, which polypeptide comprises an affinity tag fused to the Pro-domain or the Cat-domain of said polypeptide and a detectable tag fused to the other domain of said polypeptide,
 (ii) incubating said polypeptide under conditions which allow autoproteolytic cleavage of said polypeptide,
 (iii) removing polypeptides comprising the domain fused to the detectable tag which have been proteolytically cleaved from said ProCat polypeptide, optionally in the presence of a denaturant; and
 (iv) determining the domain fused to the detectable tag; wherein, said substance is determined to be an inhibitor if more of said domain fused to the detectable tag is associated with the domain fused to the affinity tag than in the absence of the substance.

11. The method of claim 10 wherein the affinity tag comprises 6 or more consecutive histidine residues and the affinity resin comprises $Ni^{2+}$ or $Co^{2+}$.

12. The method of claim 10 wherein step (iii) is performed by washing the resin with urea one or more times.

13. The method of claim 1 wherein said Pro-Cat-domain polypeptide comprises the amino acid sequence: OEDEDGDYEELVLALRSEEDGLAEAPEHGT-TATFHRCAKDPWRLPGTYVVVLKEETHL-SOSERTARRLQAQ AARRGYLTKILHVFHGLLPGFLVKMS-GDLLELALKLPHVDYIEEDSSVFAQSIP-WNLERITPPRYRADEYQ PPDGGSLVEVYLLDTSIQS-DHREIEGRVMVTDFENVPEEDGTREHRQASKCDSH-GTHLAGVVSGRDAGVAK GASMRSLRVLNC-QGKGTVSGTLIGLEFIRKSOLVQPVG-PLVVLLPLAGGYSRVLNAACORLARAGVVLVTA AGNFRDDACLYSPASAPEVITVGAT-NAQDQPVTLGTLGTNFGRCVDLFAPGE-DIIGASSDCSTCFVSQSGT SQAAAHVAGIAAMML-SAEPELTLAELRQRLIHFSAKDVINEAWFPEDQRVLT-PNLVAALPPSTHGAGWQ (SEQ ID NO: 10).

14. The method of claim 1 wherein the mixture is incubated at about 25° C. and comprises 25 mM Hepes pH 7.5, 150 mM NaCl, 10% glycerol and 1 mM EDTA.

15. A method for identifying a substance for:
 reducing total cholesterol level in the body of a subject;
 reducing low density lipoprotein cholesterol level in the body of a subject;
 reducing apolipoprotein B level in the body of a subject;
 reducing total cholesterol/high density lipoprotein ratio in the body of a subject; or
 reducing low density lipoprotein/high density lipoprotein ratio in the body of a subject;
 or for treating a medical disorder, in a subject, selected from the group consisting of:
 hypercholesterolemia;
 hyperlipidemia;
 hypertriglyceridaemia;
 sitosterolemia;
 atherosclerosis;
 arteriosclerosis;

coronary heart disease;
vascular inflammation; and
xanthoma;
comprising identifying an inhibitor of PCSK9 by the method of claim 1.

16. The method of claim 1 which is performed in association with a negative-control assay comprising incubating a mixture comprising a polypeptide comprising a PCSK9 Pro-Cat-domain under conditions which allow autoproteolytic cleavage of the polypeptide between the Pro-domain and the Cat-domain in the presence of a substance known not to be an inhibitor of PCSK9 autoproteolysis; and determining generation of said Pro-domain or said Cat-domain, or both; wherein the quantity of Pro-domain or Cat-domain, or both, indicates the maximum amount of proteolysis.

17. The method of claim 16 wherein said maximum amount of proteolysis is compared to the level that is observed in the presence of the substance to be tested for inhibition of said PCSK9; and wherein the substance is identified as the inhibitor if generation of the domain(s) occur(s) at a lower level, in the presence of the substance to be tested for inhibition of said PCSK9, than that of the maximum amount of proteolysis observed in the negative-control assay.

18. The method of claim 1 which is performed in association with a positive-control assay comprising incubating a mixture comprising a polypeptide comprising a PCSK9 Pro-Cat-domain under conditions which allow autoproteolytic cleavage of the polypeptide between the Pro-domain and Cat-domain in the presence of a positive-control substance known to be an inhibitor of PCSK9 autoproteolysis; and determining generation of said Pro-domain or said Cat-domain, or both, wherein the assay is determined to be functioning properly if generation of said domain(s) occur(s) at a lower level than that observed in the absence of said positive-control substance.

19. The method of claim 1 wherein PCSK9 is human PCSK9, chimp PCSK9, mouse PCSK9 or rat PCSK9.

20. The method of claim 19 wherein the PCSK9 comprises the ProCat-domain of human PCSK9, chimp PCSK9, mouse PCSK9 or rat PCSK9.

* * * * *

SEQUENCE LISTING

```
<160> NUMBER OF SEQ ID NOS: 13

<210> SEQ ID NO 1
<211> LENGTH: 692
<212> TYPE: PRT
<213> ORGANISM: Homo sapiens
<220> FEATURE:
<221> NAME/KEY: VARIANT
<222> LOCATION: (46)..(46)
<223> OTHER INFORMATION: Leucine
<220> FEATURE:
<221> NAME/KEY: VARIANT
<222> LOCATION: (127)..(127)
<223> OTHER INFORMATION: Arginine
<220> FEATURE:
<221> NAME/KEY: VARIANT
<222> LOCATION: (215)..(215)
<223> OTHER INFORMATION: Histidine
<220> FEATURE:
<221> NAME/KEY: VARIANT
<222> LOCATION: (236)..(236)
<223> OTHER INFORMATION: Serine
<220> FEATURE:
<221> NAME/KEY: VARIANT
<222> LOCATION: (245)..(245)
<223> OTHER INFORMATION: Threonine
<220> FEATURE:
<221> NAME/KEY: VARIANT
<222> LOCATION: (272)..(272)
<223> OTHER INFORMATION: Glutamine
<220> FEATURE:
<221> NAME/KEY: VARIANT
<222> LOCATION: (354)..(354)
<223> OTHER INFORMATION: Isoleucine
<220> FEATURE:
<221> NAME/KEY: VARIANT
<222> LOCATION: (374)..(374)
<223> OTHER INFORMATION: Tyrosine

<400> SEQUENCE: 1

Met Gly Thr Val Ser Ser Arg Arg Ser Trp Trp Pro Leu Pro Leu Leu
 1               5                  10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
            35                  40                  45

Glu Asp Gly Leu Ala Glu Ala Pro Glu His Gly Thr Thr Ala Thr Phe
        50                  55                  60

His Arg Cys Ala Lys Asp Pro Trp Arg Leu Pro Gly Thr Tyr Val Val
 65                  70                  75                  80
```

```
Val Leu Lys Glu Glu Thr His Leu Ser Gln Ser Glu Arg Thr Ala Arg
                85                  90                  95

Arg Leu Gln Ala Gln Ala Arg Arg Gly Tyr Leu Thr Lys Ile Leu
            100                 105                 110

His Val Phe His Gly Leu Leu Pro Gly Phe Leu Val Lys Met Ser Gly
            115                 120                 125

Asp Leu Leu Glu Leu Ala Leu Lys Leu Pro His Val Asp Tyr Ile Glu
130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
            195                 200                 205

Pro Glu Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
            275                 280                 285

Leu Ala Gly Gly Tyr Ser Arg Val Leu Asn Ala Ala Cys Gln Arg Leu
290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
            355                 360                 365

Ile Gly Ala Ser Ser Asp Cys Ser Thr Cys Phe Val Ser Gln Ser Gly
370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Leu Pro Pro Ser Thr
            435                 440                 445

His Gly Ala Gly Trp Gln Leu Phe Cys Arg Thr Val Trp Ser Ala His
            450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
```

```
                500             505             510
Asn Ala Phe Gly Gly Glu Gly Val Tyr Ala Ile Ala Arg Cys Cys Leu
            515                 520                 525
Leu Pro Gln Ala Asn Cys Ser Val His Thr Ala Pro Pro Ala Glu Ala
            530                 535                 540
Ser Met Gly Thr Arg Val His Cys His Gln Gln Gly His Val Leu Thr
545                 550                 555                 560
Gly Cys Ser Ser His Trp Glu Val Glu Asp Leu Gly Thr His Lys Pro
                565                 570                 575
Pro Val Leu Arg Pro Arg Gly Gln Pro Asn Gln Cys Val Gly His Arg
            580                 585                 590
Glu Ala Ser Ile His Ala Ser Cys Cys His Ala Pro Gly Leu Glu Cys
            595                 600                 605
Lys Val Lys Glu His Gly Ile Pro Ala Pro Gln Glu Gln Val Thr Val
            610                 615                 620
Ala Cys Glu Glu Gly Trp Thr Leu Thr Gly Cys Ser Ala Leu Pro Gly
625                 630                 635                 640
Thr Ser His Val Leu Gly Ala Tyr Ala Val Asp Asn Thr Cys Val Val
                645                 650                 655
Arg Ser Arg Asp Val Ser Thr Thr Gly Ser Thr Ser Glu Gly Ala Val
            660                 665                 670
Thr Ala Val Ala Ile Cys Cys Arg Ser Arg His Leu Ala Gln Ala Ser
            675                 680                 685
Gln Glu Leu Gln
        690

<210> SEQ ID NO 2
<211> LENGTH: 677
<212> TYPE: PRT
<213> ORGANISM: Pan troglodytes

<400> SEQUENCE: 2

Met Gly Thr Val Ser Ser Arg Arg Ser Trp Trp Pro Leu Pro Leu Leu
1               5                   10                  15
Leu Leu Leu Leu Leu Leu Leu Gly Pro Ala Gly Ala Arg Ala Gln Glu
            20                  25                  30
Asp Glu Asp Gly Leu Ala Glu Ala Pro Glu His Gly Thr Thr Ala Thr
            35                  40                  45
Phe His Arg Cys Ala Lys Asp Pro Trp Arg Leu Pro Gly Thr Tyr Val
            50                  55                  60
Val Val Leu Lys Glu Glu Thr His Leu Ser Gln Ser Glu Arg Thr Ala
65                  70                  75                  80
Arg Arg Leu Gln Ala Gln Ala Ala Arg Arg Gly Tyr Leu Thr Lys Ile
            85                  90                  95
Leu His Val Phe His Gly Leu Leu Pro Gly Phe Leu Val Lys Met Ser
            100                 105                 110
Gly Asp Leu Leu Glu Leu Ala Leu Lys Leu Pro His Val Asp Tyr Ile
            115                 120                 125
Glu Glu Asp Ser Ser Val Phe Ala Gln Ser Ile Pro Trp Asn Leu Glu
            130                 135                 140
Arg Ile Thr Pro Pro Arg Tyr Arg Ala Asp Glu Tyr Gln Pro Pro Asp
145                 150                 155                 160
Gly Gly Ser Leu Val Glu Val Tyr Leu Leu Asp Thr Ser Ile Gln Ser
                165                 170                 175
Asp His Arg Glu Ile Glu Gly Arg Val Met Val Thr Asp Phe Glu Asn
```

```
                180             185              190
Val Pro Glu Glu Asp Gly Thr Arg Phe His Arg Gln Ala Ser Lys Cys
            195                 200                 205

Asp Ser His Gly Thr His Leu Ala Gly Val Val Ser Gly Arg Asp Ala
            210                 215                 220

Gly Val Ala Lys Gly Ala Ser Met Arg Ser Leu Arg Val Leu Asn Cys
225                 230                 235                 240

Gln Gly Lys Gly Thr Val Ser Gly Thr Leu Ile Gly Leu Glu Phe Ile
            245                 250                 255

Arg Lys Ser Gln Leu Val Gln Pro Val Gly Pro Leu Val Leu Leu
            260                 265                 270

Pro Leu Ala Gly Gly Tyr Ser Arg Val Leu Asn Ala Ala Cys Gln Arg
            275                 280                 285

Leu Ala Arg Ala Gly Val Val Leu Val Thr Ala Ala Gly Asn Phe Arg
            290                 295                 300

Asp Asp Ala Cys Leu Tyr Ser Pro Ala Ser Ala Pro Glu Val Ile Thr
305                 310                 315                 320

Val Gly Ala Thr Asn Ala Gln Asp Gln Pro Val Thr Leu Gly Thr Leu
            325                 330                 335

Gly Thr Asn Phe Gly Arg Cys Val Asp Leu Phe Ala Pro Gly Glu Asp
            340                 345                 350

Ile Ile Gly Ala Ser Ser Asp Cys Ser Thr Cys Phe Val Ser Gln Ser
            355                 360                 365

Gly Thr Ser Gln Ala Ala Ala His Val Ala Gly Ile Ala Ala Met Met
            370                 375                 380

Leu Ser Ala Glu Pro Glu Leu Thr Leu Ala Glu Leu Arg Gln Arg Leu
385                 390                 395                 400

Ile His Phe Ser Ala Lys Asp Val Ile Asn Glu Ala Trp Phe Pro Glu
            405                 410                 415

Asp Gln Arg Val Leu Thr Pro Asn Leu Val Ala Ala Leu Pro Pro Ser
            420                 425                 430

Thr His Gly Ala Gly Trp Gln Leu Phe Cys Arg Thr Val Trp Ser Ala
            435                 440                 445

His Ser Gly Pro Thr Arg Met Ala Thr Ala Val Ala Arg Cys Ala Pro
450                 455                 460

Asp Glu Glu Leu Leu Ser Cys Ser Ser Phe Ser Arg Ser Gly Lys Arg
465                 470                 475                 480

Arg Gly Glu Arg Met Glu Ala Gln Gly Gly Lys Leu Val Cys Arg Ala
            485                 490                 495

His Asn Ala Phe Gly Gly Glu Gly Val Tyr Ala Ile Ala Arg Cys Cys
            500                 505                 510

Leu Leu Pro Gln Ala Asn Cys Ser Ile His Thr Ala Pro Pro Ala Glu
            515                 520                 525

Ala Gly Met Gly Thr Arg Val His Cys His Gln Gly His Val Leu
            530                 535                 540

Thr Gly Cys Ser Ser His Trp Glu Val Glu Asp Leu Gly Thr His Lys
545                 550                 555                 560

Pro Pro Met Leu Arg Pro Arg Gly Gln Pro Asn Gln Cys Val Gly His
            565                 570                 575

Arg Glu Ala Ser Ile His Ala Ser Cys Cys Arg Ala Pro Gly Leu Glu
            580                 585                 590

Cys Lys Val Lys Glu His Gly Ile Pro Ala Pro Gln Glu Gln Val Thr
            595                 600                 605
```

```
Val Ala Cys Glu Glu Gly Trp Thr Leu Thr Gly Cys Ser Ala Leu Pro
    610                 615                 620

Gly Thr Ser His Val Leu Gly Ala Tyr Ala Val Asp Asn Thr Cys Val
625                 630                 635                 640

Val Arg Ser Arg Asp Val Ser Thr Ala Gly Ser Thr Ser Glu Glu Ala
            645                 650                 655

Val Ala Ala Val Ala Ile Cys Cys Arg Ser Arg His Leu Ala Gln Ala
        660                 665                 670

Ser Gln Glu Leu Gln
        675

<210> SEQ ID NO 3
<211> LENGTH: 694
<212> TYPE: PRT
<213> ORGANISM: Mus musculus

<400> SEQUENCE: 3

Met Gly Thr His Cys Ser Ala Trp Leu Arg Trp Pro Leu Leu Pro Leu
1               5                   10                  15

Leu Pro Pro Leu Leu Leu Leu Leu Leu Leu Cys Pro Thr Gly Ala
                20                  25                  30

Gly Ala Gln Asp Glu Asp Gly Asp Tyr Glu Glu Leu Met Leu Ala Leu
            35                  40                  45

Pro Ser Gln Glu Asp Gly Leu Ala Asp Glu Ala Ala His Val Ala Thr
50                  55                  60

Ala Thr Phe Arg Arg Cys Ser Lys Glu Ala Trp Arg Leu Pro Gly Thr
65                  70                  75                  80

Tyr Ile Val Val Leu Met Glu Glu Thr Gln Arg Leu Gln Ile Glu Gln
                85                  90                  95

Thr Ala His Arg Leu Gln Thr Arg Ala Ala Arg Arg Gly Tyr Val Ile
            100                 105                 110

Lys Val Leu His Ile Phe Tyr Asp Leu Phe Pro Gly Phe Leu Val Lys
        115                 120                 125

Met Ser Ser Asp Leu Leu Gly Leu Ala Leu Lys Leu Pro His Val Glu
    130                 135                 140

Tyr Ile Glu Glu Asp Ser Phe Val Phe Ala Gln Ser Ile Pro Trp Asn
145                 150                 155                 160

Leu Glu Arg Ile Ile Pro Ala Trp His Gln Thr Glu Glu Asp Arg Ser
                165                 170                 175

Pro Asp Gly Ser Ser Gln Val Glu Val Tyr Leu Leu Asp Thr Ser Ile
            180                 185                 190

Gln Gly Ala His Arg Glu Ile Glu Gly Arg Val Thr Ile Thr Asp Phe
        195                 200                 205

Asn Ser Val Pro Glu Glu Asp Gly Thr Arg Phe His Arg Gln Ala Ser
    210                 215                 220

Lys Cys Asp Ser His Gly Thr His Leu Ala Gly Val Val Ser Gly Arg
225                 230                 235                 240

Asp Ala Gly Val Ala Lys Gly Thr Ser Leu His Ser Leu Arg Val Leu
                245                 250                 255

Asn Cys Gln Gly Lys Gly Thr Val Ser Gly Thr Leu Ile Gly Leu Glu
            260                 265                 270

Phe Ile Arg Lys Ser Gln Leu Ile Gln Pro Ser Gly Pro Leu Val Val
        275                 280                 285

Leu Leu Pro Leu Ala Gly Gly Tyr Ser Arg Ile Leu Asn Ala Ala Cys
    290                 295                 300
```

```
Arg His Leu Ala Arg Thr Gly Val Val Leu Val Ala Ala Ala Gly Asn
305                 310                 315                 320

Phe Arg Asp Asp Ala Cys Leu Tyr Ser Pro Ala Ser Ala Pro Glu Val
            325                 330                 335

Ile Thr Val Gly Ala Thr Asn Ala Gln Asp Gln Pro Val Thr Leu Gly
        340                 345                 350

Thr Leu Gly Thr Asn Phe Gly Arg Cys Val Asp Leu Phe Ala Pro Gly
    355                 360                 365

Lys Asp Ile Ile Gly Ala Ser Ser Asp Cys Ser Thr Cys Phe Met Ser
370                 375                 380

Gln Ser Gly Thr Ser Gln Ala Ala Ala His Val Ala Gly Ile Val Ala
385                 390                 395                 400

Arg Met Leu Ser Arg Glu Pro Thr Leu Thr Leu Ala Glu Leu Arg Gln
            405                 410                 415

Arg Leu Ile His Phe Ser Thr Lys Asp Val Ile Asn Met Ala Trp Phe
        420                 425                 430

Pro Glu Asp Gln Gln Val Leu Thr Pro Asn Leu Val Ala Thr Leu Pro
            435                 440                 445

Pro Ser Thr His Glu Thr Gly Gly Gln Leu Leu Cys Arg Thr Val Trp
450                 455                 460

Ser Ala His Ser Gly Pro Thr Arg Thr Ala Thr Ala Thr Ala Arg Cys
465                 470                 475                 480

Ala Pro Glu Glu Glu Leu Leu Ser Cys Ser Ser Phe Ser Arg Ser Gly
            485                 490                 495

Arg Arg Arg Gly Asp Trp Ile Glu Ala Ile Gly Gly Gln Gln Val Cys
            500                 505                 510

Lys Ala Leu Asn Ala Phe Gly Gly Glu Gly Val Tyr Ala Val Ala Arg
515                 520                 525

Cys Cys Leu Val Pro Arg Ala Asn Cys Ser Ile His Asn Thr Pro Ala
            530                 535                 540

Ala Arg Ala Gly Leu Glu Thr His Val His Cys His Gln Lys Asp His
545                 550                 555                 560

Val Leu Thr Gly Cys Ser Phe His Trp Glu Val Glu Asp Leu Ser Val
            565                 570                 575

Arg Arg Gln Pro Ala Leu Arg Ser Arg Gln Pro Gly Gln Cys Val
            580                 585                 590

Gly His Gln Ala Ala Ser Val Tyr Ala Ser Cys Cys His Ala Pro Gly
            595                 600                 605

Leu Glu Cys Lys Ile Lys Glu His Gly Ile Ser Gly Pro Ser Glu Gln
            610                 615                 620

Val Thr Val Ala Cys Glu Ala Gly Trp Thr Leu Thr Gly Cys Asn Val
625                 630                 635                 640

Leu Pro Gly Ala Ser Leu Thr Leu Gly Ala Tyr Ser Val Asp Asn Leu
            645                 650                 655

Cys Val Ala Arg Val His Asp Thr Ala Arg Ala Asp Arg Thr Ser Gly
            660                 665                 670

Glu Ala Thr Val Ala Ala Ile Cys Cys Arg Ser Arg Pro Ser Ala
            675                 680                 685

Lys Ala Ser Trp Val Gln
    690

<210> SEQ ID NO 4
<211> LENGTH: 691
<212> TYPE: PRT
<213> ORGANISM: Rattus norvegicus
```

-continued

```
<400> SEQUENCE: 4

Met Gly Ile Arg Cys Ser Thr Trp Leu Arg Trp Pro Leu Ser Pro Gln
1               5                   10                  15

Leu Leu Leu Leu Leu Leu Leu Cys Pro Thr Gly Ser Arg Ala Gln Asp
            20                  25                  30

Glu Asp Gly Asp Tyr Glu Glu Leu Met Leu Ala Leu Pro Ser Gln Glu
        35                  40                  45

Asp Ser Leu Val Asp Glu Ala Ser His Val Ala Thr Ala Thr Phe Arg
    50                  55                  60

Arg Cys Ser Lys Glu Ala Trp Arg Leu Pro Gly Thr Tyr Val Val Val
65                  70                  75                  80

Leu Met Glu Glu Thr Gln Arg Leu Gln Val Glu Gln Thr Ala His Arg
                85                  90                  95

Leu Gln Thr Trp Ala Ala Arg Gly Tyr Val Ile Lys Val Leu His
            100                 105                 110

Val Phe Tyr Asp Leu Phe Pro Gly Phe Leu Val Lys Met Ser Ser Asp
        115                 120                 125

Leu Leu Gly Leu Ala Leu Lys Leu Pro His Val Glu Tyr Ile Glu Glu
    130                 135                 140

Asp Ser Leu Val Phe Ala Gln Ser Ile Pro Trp Asn Leu Glu Arg Ile
145                 150                 155                 160

Ile Pro Ala Trp Gln Gln Thr Glu Glu Asp Ser Ser Pro Asp Gly Ser
                165                 170                 175

Ser Gln Val Glu Val Tyr Leu Leu Asp Thr Ser Ile Gln Ser Gly His
            180                 185                 190

Arg Glu Ile Glu Gly Arg Val Thr Ile Thr Asp Phe Asn Ser Val Pro
        195                 200                 205

Glu Glu Asp Gly Thr Arg Phe His Arg Gln Ala Ser Lys Cys Asp Ser
    210                 215                 220

His Gly Thr His Leu Ala Gly Val Val Ser Gly Arg Asp Ala Gly Val
225                 230                 235                 240

Ala Lys Gly Thr Ser Leu His Ser Leu Arg Val Leu Asn Cys Gln Gly
                245                 250                 255

Lys Gly Thr Val Ser Gly Thr Leu Ile Gly Leu Glu Phe Ile Arg Lys
            260                 265                 270

Ser Gln Leu Ile Gln Pro Ser Gly Pro Leu Val Val Leu Leu Pro Leu
        275                 280                 285

Ala Gly Gly Tyr Ser Arg Ile Leu Asn Thr Ala Cys Gln Arg Leu Ala
    290                 295                 300

Arg Thr Gly Val Val Leu Val Ala Ala Ala Gly Asn Phe Arg Asp Asp
305                 310                 315                 320

Ala Cys Leu Tyr Ser Pro Ala Ser Ala Pro Glu Val Ile Thr Val Gly
                325                 330                 335

Ala Thr Asn Ala Gln Asp Gln Pro Val Thr Leu Gly Thr Leu Gly Thr
            340                 345                 350

Asn Phe Gly Arg Cys Val Asp Leu Phe Ala Pro Gly Lys Asp Ile Ile
        355                 360                 365

Gly Ala Ser Ser Asp Cys Ser Thr Cys Tyr Met Ser Gln Ser Gly Thr
    370                 375                 380

Ser Gln Ala Ala Ala His Val Ala Gly Ile Val Ala Met Met Leu Asn
385                 390                 395                 400

Arg Asp Pro Ala Leu Thr Leu Ala Glu Leu Arg Gln Arg Leu Ile Leu
                405                 410                 415
```

```
Phe Ser Thr Lys Asp Val Ile Asn Met Ala Trp Phe Pro Glu Asp Gln
            420                 425                 430

Arg Val Leu Thr Pro Asn Arg Val Ala Thr Leu Pro Pro Ser Thr Gln
            435                 440                 445

Glu Thr Gly Gly Gln Leu Leu Cys Arg Thr Val Trp Ser Ala His Ser
    450                 455                 460

Gly Pro Thr Arg Thr Ala Thr Ala Thr Ala Arg Cys Ala Pro Glu Glu
465                 470                 475                 480

Glu Leu Leu Ser Cys Ser Ser Phe Ser Arg Ser Gly Arg Arg Gly
                485                 490                 495

Asp Arg Ile Glu Ala Ile Gly Gly Gln Val Cys Lys Ala Leu Asn
                500                 505                 510

Ala Phe Gly Gly Glu Gly Val Tyr Ala Val Ala Arg Cys Cys Leu Leu
            515                 520                 525

Pro Arg Val Asn Cys Ser Ile His Asn Thr Pro Ala Ala Arg Ala Gly
            530                 535                 540

Pro Gln Thr Pro Val His Cys His Gln Lys Asp His Val Leu Thr Gly
545                 550                 555                 560

Cys Ser Phe His Trp Glu Val Glu Asn Leu Arg Ala Gln Gln Pro
                565                 570                 575

Leu Leu Arg Ser Arg His Gln Pro Gly Gln Cys Val Gly His Gln Glu
            580                 585                 590

Ala Ser Val His Ala Ser Cys Cys His Ala Pro Gly Leu Glu Cys Lys
            595                 600                 605

Ile Lys Glu His Gly Ile Ala Gly Pro Ala Glu Gln Val Thr Val Ala
            610                 615                 620

Cys Glu Ala Gly Trp Thr Leu Thr Gly Cys Asn Val Leu Pro Gly Ala
625                 630                 635                 640

Ser Leu Pro Leu Gly Ala Tyr Ser Val Asp Asn Val Cys Val Ala Arg
                645                 650                 655

Ile Arg Asp Ala Gly Arg Ala Asp Arg Thr Ser Glu Glu Ala Thr Val
                660                 665                 670

Ala Ala Ala Ile Cys Cys Arg Ser Arg Pro Ser Ala Lys Ala Ser Trp
            675                 680                 685

Val His Gln
    690

<210> SEQ ID NO 5
<211> LENGTH: 32
<212> TYPE: DNA
<213> ORGANISM: Artificial Sequence
<220> FEATURE:
<223> OTHER INFORMATION: Pro(+) primer

<400> SEQUENCE: 5
caccatgcaa gaggatgaag atggagacta tg                                  32

<210> SEQ ID NO 6
<211> LENGTH: 44
<212> TYPE: DNA
<213> ORGANISM: Artificial  Sequence
<220> FEATURE:
<223> OTHER INFORMATION: Cat(-) primer

<400> SEQUENCE: 6
ctaatgatgg tgatggtggt gagatccctg ccagcctgcc ccgt                     44
```

-continued

<210> SEQ ID NO 7
<211> LENGTH: 1275
<212> TYPE: DNA
<213> ORGANISM: Homo sapiens

<400> SEQUENCE: 7

| | | | | | |
|---|---|---|---|---|---|
| atgcaagagg | atgaagatgg | agactatgag | gagctggtcc | tggcttttgcg | atctgaagaa | 60 |
| gacggactgg | ccgaggcccc | agagcatggg | actactgcga | cctttcacag | gtgtgcaaaa | 120 |
| gaccccttgga | ggctgcccgg | gacttacgtt | gtggttctga | aggaagaaac | tcacttgagc | 180 |
| caatccgaac | gaacagcccg | gcggttgcaa | gcccaggctg | cgcgccgcgg | gtatttgact | 240 |
| aagatccttc | atgtgttcca | tggcctgctg | ccagggttcc | tggtcaagat | gagcggggat | 300 |
| cttctcgagc | tggcgctgaa | gctgcctcac | gtagactata | tcgaggaaga | tagctctgtg | 360 |
| ttcgctcaga | gcatcccttg | gaacttggag | agaatcaccc | ccccagata | tcgagctgac | 420 |
| gagtaccaac | caccggacgg | gggctccctg | gtggaagtct | acttgctgga | caccagtatt | 480 |
| cagtctgacc | atagggagat | cgagggtcgg | gtcatggtga | ccgactttga | aacgtccca | 540 |
| gaagaagacg | gacgagatt | tcaccgccag | gccagtaagt | gtgactcaca | cggaacgcat | 600 |
| ctggctggtg | ttgtcagtgg | gagggacgca | ggtgtggcta | agggcgccag | catgcgcagc | 660 |
| ctgagagtgc | tcaattgcca | ggggaagggg | accgtgagtg | gaactctgat | tggactggag | 720 |
| ttcattagga | agagccagct | ggtgcagccg | gtgggcccct | tggtggtatt | gctgcccctg | 780 |
| gcaggagggt | atagccgggt | gcttaatgcc | gcctgtcaga | ggctggccag | agccggcgtt | 840 |
| gttctggtga | ctgccgccgg | aaatttccgg | gacgatgctt | gcttgtacag | cccagcgagc | 900 |
| gctccggaag | tgatcacagt | aggcgcaacg | aacgcccagg | atcagcctgt | aaccctgggg | 960 |
| actctgggaa | ccaactttgg | acggtgtgtc | gatctttttg | ctcccggaga | ggatatattc | 1020 |
| ggagcatcct | cagattgttc | cacctgcttt | gtatcccaga | gcggaacctc | tcaggcagct | 1080 |
| gcacacgttg | ctggaattgc | cgctatgatg | ttgtctgccg | agccggagct | cacattggcc | 1140 |
| gagctgagac | agcgcttgat | tcacttcagc | gcgaaagatg | tgataaatga | ggcctggttt | 1200 |
| ccagaggacc | aacgagttct | gaccccccaac | ctggtggctg | cactgccacc | ttctacccac | 1260 |
| ggggcaggct | ggcag | | | | | 1275 |

<210> SEQ ID NO 8
<211> LENGTH: 123
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Methionine added to amino acid sequence of
       mature PCSK9 propeptide

<400> SEQUENCE: 8

```
Met Gln Glu Asp Glu Asp Gly Asp Tyr Glu Glu Leu Val Leu Ala Leu
 1               5                  10                  15

Arg Ser Glu Glu Asp Gly Leu Ala Glu Ala Pro Glu His Gly Thr Thr
            20                  25                  30

Ala Thr Phe His Arg Cys Ala Lys Asp Pro Trp Arg Leu Pro Gly Thr
        35                  40                  45

Tyr Val Val Val Leu Lys Glu Glu Thr His Leu Ser Gln Ser Glu Arg
    50                  55                  60

Thr Ala Arg Arg Leu Gln Ala Gln Ala Ala Arg Arg Gly Tyr Leu Thr
65                  70                  75                  80

Lys Ile Leu His Val Phe His Gly Leu Leu Pro Gly Phe Leu Val Lys
```

```
                         85                  90                  95
Met Ser Gly Asp Leu Leu Glu Leu Ala Leu Lys Leu Pro His Val Asp
            100                 105                 110
Tyr Ile Glu Glu Asp Ser Ser Val Phe Ala Gln
            115                 120

<210> SEQ ID NO 9
<211> LENGTH: 310
<212> TYPE: PRT
<213> ORGANISM: Homo sapiens
<220> FEATURE:
<221> NAME/KEY: MISC_FEATURE
<222> LOCATION: (303)..(310)
<223> OTHER INFORMATION: GS linker-Hexahistidine tag

<400> SEQUENCE: 9

Ser Ile Pro Trp Asn Leu Glu Arg Ile Thr Pro Pro Arg Tyr Arg Ala
1               5                   10                  15
Asp Glu Tyr Gln Pro Pro Asp Gly Gly Ser Leu Val Glu Val Tyr Leu
            20                  25                  30
Leu Asp Thr Ser Ile Gln Ser Asp His Arg Glu Ile Glu Gly Arg Val
        35                  40                  45
Met Val Thr Asp Phe Glu Asn Val Pro Glu Glu Asp Gly Thr Arg Phe
    50                  55                  60
His Arg Gln Ala Ser Lys Cys Asp Ser His Gly Thr His Leu Ala Gly
65                  70                  75                  80
Val Val Ser Gly Arg Asp Ala Gly Val Ala Lys Gly Ala Ser Met Arg
                85                  90                  95
Ser Leu Arg Val Leu Asn Cys Gln Gly Lys Gly Thr Val Ser Gly Thr
            100                 105                 110
Leu Ile Gly Leu Glu Phe Ile Arg Lys Ser Gln Leu Val Gln Pro Val
        115                 120                 125
Gly Pro Leu Val Val Leu Leu Pro Leu Ala Gly Gly Tyr Ser Arg Val
    130                 135                 140
Leu Asn Ala Ala Cys Gln Arg Leu Ala Arg Ala Gly Val Val Leu Val
145                 150                 155                 160
Thr Ala Ala Gly Asn Phe Arg Asp Asp Ala Cys Leu Tyr Ser Pro Ala
                165                 170                 175
Ser Ala Pro Glu Val Ile Thr Val Gly Ala Thr Asn Ala Gln Asp Gln
            180                 185                 190
Pro Val Thr Leu Gly Thr Leu Gly Thr Asn Phe Gly Arg Cys Val Asp
        195                 200                 205
Leu Phe Ala Pro Gly Glu Asp Ile Ile Gly Ala Ser Ser Asp Cys Ser
    210                 215                 220
Thr Cys Phe Val Ser Gln Ser Gly Thr Ser Gln Ala Ala Ala His Val
225                 230                 235                 240
Ala Gly Ile Ala Ala Met Met Leu Ser Ala Glu Pro Glu Leu Thr Leu
                245                 250                 255
Ala Glu Leu Arg Gln Arg Leu Ile His Phe Ser Ala Lys Asp Val Ile
            260                 265                 270
Asn Glu Ala Trp Phe Pro Glu Asp Gln Arg Val Leu Thr Pro Asn Leu
        275                 280                 285
Val Ala Ala Leu Pro Pro Ser Thr His Gly Ala Gly Trp Gln Gly Ser
    290                 295                 300
His His His His His His
305                 310
```

<210> SEQ ID NO 10
<211> LENGTH: 432
<212> TYPE: PRT
<213> ORGANISM: Homo sapiens
<220> FEATURE:
<221> NAME/KEY: MISC_FEATURE
<222> LOCATION: (425)..(432)
<223> OTHER INFORMATION: GS linker-Hexahistidine tag

<400> SEQUENCE: 10

Gln Glu Asp Glu Asp Gly Asp Tyr Glu Glu Leu Val Leu Ala Leu Arg
1               5                   10                  15

Ser Glu Glu Asp Gly Leu Ala Glu Ala Pro Glu His Gly Thr Thr Ala
            20                  25                  30

Thr Phe His Arg Cys Ala Lys Asp Pro Trp Arg Leu Pro Gly Thr Tyr
        35                  40                  45

Val Val Val Leu Lys Glu Glu Thr His Leu Ser Gln Ser Glu Arg Thr
    50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
                85                  90                  95

Ser Gly Asp Leu Leu Glu Leu Ala Leu Lys Leu Pro His Val Asp Tyr
            100                 105                 110

Ile Glu Glu Asp Ser Ser Val Phe Ala Gln Ser Ile Pro Trp Asn Leu
        115                 120                 125

Glu Arg Ile Thr Pro Pro Arg Tyr Arg Ala Asp Glu Tyr Gln Pro Pro
    130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
        195                 200                 205

Ala Gly Val Ala Lys Gly Ala Ser Met Arg Ser Leu Arg Val Leu Asn
    210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                245                 250                 255

Leu Pro Leu Ala Gly Gly Tyr Ser Arg Val Leu Asn Ala Ala Cys Gln
            260                 265                 270

Arg Leu Ala Arg Ala Gly Val Val Leu Val Thr Ala Ala Gly Asn Phe
        275                 280                 285

Arg Asp Asp Ala Cys Leu Tyr Ser Pro Ala Ser Ala Pro Glu Val Ile
    290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Glu
                325                 330                 335

Asp Ile Ile Gly Ala Ser Ser Asp Cys Ser Thr Cys Phe Val Ser Gln
            340                 345                 350

Ser Gly Thr Ser Gln Ala Ala Ala His Val Ala Gly Ile Ala Ala Met
        355                 360                 365

```
Met Leu Ser Ala Glu Pro Glu Leu Thr Leu Ala Glu Leu Arg Gln Arg
        370             375                 380

Leu Ile His Phe Ser Ala Lys Asp Val Ile Asn Glu Ala Trp Phe Pro
385             390                 395                 400

Glu Asp Gln Arg Val Leu Thr Pro Asn Leu Val Ala Ala Leu Pro Pro
                405                 410                 415

Ser Thr His Gly Ala Gly Trp Gln Gly Ser His His His His His His
            420                 425                 430

<210> SEQ ID NO 11
<211> LENGTH: 1373
<212> TYPE: DNA
<213> ORGANISM: Homo sapiens

<400> SEQUENCE: 11
gcggccgcct tgtttaactt taagaaggag cccttcacca tggattataa ggacgacgat    60
gataagcaag aggatgaaga tggagactat gaggagctgg tcctggcttt gcgatctgaa   120
gaagacggac tggccgaggc ccagagcatg ggactactg cgacctttca caggtgtgca    180
aaagacccct tggaggctgc cggagactac gttgtggttc tgaaggaaga aactcacttg   240
agccaatccg aacgaacagc ccggcggttg caagcccagg ctgcgcgccg cgggtatttg   300
actaagatcc ttcatgtgtt ccatggcctg ctgccagggt tcctggtcaa gatgagcggg   360
gatcttctcg agctggcgct gaagctgcct cacgtagact atatcgagga agatagctct   420
gtgttcgctc agagcatccc ttggaacttg agagaatca cccccccag atatcgagct    480
gacgagtacc aaccaccgga cggggggctcc ctggtggaag tctacttgct ggacaccagt   540
attcagtctg accataggga gatcgagggt cgggtcatgg tgaccgactt tgagaacgtc   600
ccagaagaag acgggacgag atttcaccgc caggccagta agtgtgactc acacggaacg   660
catctggctg tgttgtcag tgggagggac gcaggtgtgg ctaagggcgc cagcatgcgc   720
agcctgagag tgctcaattg ccaggggaag gggaccgtga gtggaactct gattggactg   780
gagttcatta ggaagagcca gctggtgcag ccggtgggcc ccttggtggt attgctgccc   840
ctggcaggag ggtatagccg ggtgcttaat gccgcctgtc agaggctggc cagagccggc   900
gttgttctgg tgactgccgc cggaaatttc cgggacgatg cttgcttgta cagcccagcg   960
agcgctccgg aagtgatcac agtaggcgca acgaacgccc aggatcagcc tgtaaccctg  1020
gggactctgg gaaccaactt tggacggtgt gtcgatcttt ttgctcccgg agaggatatt  1080
atcggagcat cctcagattg ttccacctgc tttgtatccc agagcggaac ctctcaggca  1140
gctgcacacg ttgctggaat tgccgctatg atgttgtctg ccgagccgga gctcacattg  1200
gccgagctga cagcgcttt gattcacttc agcgcgaaag atgtgataaa tgaggcctgg  1260
tttccagagg accaacgagt tctgaccccc aacctggtgg ctgcactgcc accttctacc  1320
cacgggggcag gctggcaggg atctcaccac catcaccatc attagggcgc gcc         1373

<210> SEQ ID NO 12
<211> LENGTH: 131
<212> TYPE: PRT
<213> ORGANISM: Homo sapiens
<220> FEATURE:
<221> NAME/KEY: MISC_FEATURE
<222> LOCATION: (2)..(9)
<223> OTHER INFORMATION: FLAG tag

<400> SEQUENCE: 12

Met Asp Tyr Lys Asp Asp Asp Asp Lys Gln Glu Asp Glu Asp Gly Asp
```

-continued

```
                1               5                  10                 15
Tyr Glu Glu Leu Val Leu Ala Leu Arg Ser Glu Glu Asp Gly Leu Ala
                    20                  25                  30

Glu Ala Pro Glu His Gly Thr Thr Ala Thr Phe His Arg Cys Ala Lys
            35                  40                  45

Asp Pro Trp Arg Leu Pro Gly Thr Tyr Val Val Leu Lys Glu Glu
    50                  55                  60

Thr His Leu Ser Gln Ser Glu Arg Thr Ala Arg Arg Leu Gln Ala Gln
 65                 70                  75                  80

Ala Ala Arg Arg Gly Tyr Leu Thr Lys Ile Leu His Val Phe His Gly
                    85                  90                  95

Leu Leu Pro Gly Phe Leu Val Lys Met Ser Gly Asp Leu Leu Glu Leu
                100                 105                 110

Ala Leu Lys Leu Pro His Val Asp Tyr Ile Glu Glu Asp Ser Ser Val
            115                 120                 125

Phe Ala Gln
        130
```

<210> SEQ ID NO 13
<211> LENGTH: 310
<212> TYPE: PRT
<213> ORGANISM: Homo sapiens
<220> FEATURE:
<221> NAME/KEY: MISC_FEATURE
<222> LOCATION: (303)..(310)
<223> OTHER INFORMATION: GS linker-Hexahistidine tag

<400> SEQUENCE: 13

```
Ser Ile Pro Trp Asn Leu Glu Arg Ile Thr Pro Pro Arg Tyr Arg Ala
 1               5                  10                  15

Asp Glu Tyr Gln Pro Pro Asp Gly Gly Ser Leu Val Glu Val Tyr Leu
                    20                  25                  30

Leu Asp Thr Ser Ile Gln Ser Asp His Arg Glu Ile Glu Gly Arg Val
            35                  40                  45

Met Val Thr Asp Phe Glu Asn Val Pro Glu Glu Asp Gly Thr Arg Phe
    50                  55                  60

His Arg Gln Ala Ser Lys Cys Asp Ser His Gly Thr His Leu Ala Gly
 65                 70                  75                  80

Val Val Ser Gly Arg Asp Ala Gly Val Ala Lys Gly Ala Ser Met Arg
                    85                  90                  95

Ser Leu Arg Val Leu Asn Cys Gln Gly Lys Gly Thr Val Ser Gly Thr
                100                 105                 110

Leu Ile Gly Leu Glu Phe Ile Arg Lys Ser Gln Leu Val Gln Pro Val
            115                 120                 125

Gly Pro Leu Val Val Leu Leu Pro Leu Ala Gly Gly Tyr Ser Arg Val
    130                 135                 140

Leu Asn Ala Ala Cys Gln Arg Leu Ala Arg Ala Gly Val Val Leu Val
145                 150                 155                 160

Thr Ala Ala Gly Asn Phe Arg Asp Asp Ala Cys Leu Tyr Ser Pro Ala
                165                 170                 175

Ser Ala Pro Glu Val Ile Thr Val Gly Ala Thr Asn Ala Gln Asp Gln
            180                 185                 190

Pro Val Thr Leu Gly Thr Leu Gly Thr Asn Phe Gly Arg Cys Val Asp
    195                 200                 205

Leu Phe Ala Pro Gly Glu Asp Ile Ile Gly Ala Ser Ser Asp Cys Ser
    210                 215                 220
```

```
Thr Cys Phe Val Ser Gln Ser Gly Thr Ser Gln Ala Ala Ala His Val
225             230                 235                 240

Ala Gly Ile Ala Ala Met Met Leu Ser Ala Glu Pro Glu Leu Thr Leu
                245                 250                 255

Ala Glu Leu Arg Gln Arg Leu Ile His Phe Ser Ala Lys Asp Val Ile
            260             265                 270

Asn Glu Ala Trp Phe Pro Glu Asp Gln Arg Val Leu Thr Pro Asn Leu
        275                 280                 285

Val Ala Ala Leu Pro Pro Ser Thr His Gly Ala Gly Trp Gln Gly Ser
    290             295                 300

His His His His His His
305             310
```